(12) United States Patent
Bell et al.

(10) Patent No.: US 12,731,659 B2
(45) Date of Patent: Sep. 8, 2026

(54) SYSTEMS AND METHODS FOR AUTOMATING RNA EXPRESSION CALLS IN A CANCER PREDICTION PIPELINE

(71) Applicant: Tempus AI, Inc., Chicago, IL (US)

(72) Inventors: Joshua SK Bell, Chicago, IL (US); Catherine Igartua, Chicago, IL (US); Joshua Drews, Downers Grove, IL (US)

(73) Assignee: Tempus AI, Inc., Chicago, IL (US)

( * ) Notice: Subject to any disclaimer, the term of this patent is extended or adjusted under 35 U.S.C. 154(b) by 180 days.

(21) Appl. No.: 17/324,949

(22) Filed: May 19, 2021

(65) Prior Publication Data

US 2021/0272649 A1 Sep. 2, 2021

Related U.S. Application Data

(63) Continuation of application No. 17/112,877, filed on Dec. 4, 2020, now Pat. No. 11,043,283.

(Continued)

(51) Int. Cl.
*G16B 25/10* (2019.01)
*C12Q 1/6886* (2018.01)

(Continued)

(52) U.S. Cl.
CPC .......... *G16B 25/10* (2019.02); *C12Q 1/6886* (2013.01); *G16B 5/00* (2019.02); *G16B 50/30* (2019.02)

(58) Field of Classification Search
CPC ........................... G16B 25/10; G05B 23/0221
See application file for complete search history.

(56) References Cited

U.S. PATENT DOCUMENTS 11,043,283 B1 * 6/2021 Bell et al. .............. G16B 25/10
2016/0026754 A1 1/2016 Kohane

OTHER PUBLICATIONS

Müller et al., Removing Batch Effects from Longitudinal Gene Expression—Quantile Normalization Plus ComBat as Best Approach for Microarray Transcriptome Data, Jun. 2016, PLoS ONE 11(6): article No. e0156594, pp. 1-23 (Year: 2016).*

(Continued)

*Primary Examiner* — Jesse P Frumkin
*Assistant Examiner* — Theodore Charles Striegel
(74) *Attorney, Agent, or Firm* — MORGAN, LEWIS & BOCKIUS LLP

(57) ABSTRACT

Systems and methods are provided for performing quality control analysis. The method obtains, in electronic form, a batch dataset comprising, for each respective sample in a batch of samples, a corresponding plurality of sequence reads derived from the respective sample by targeted or whole transcriptome RNA sequencing and corresponding metadata for the respective sample. The method determines for the batch dataset a cohort-matched reference batch, where the cohort-matched reference batch is balanced for tissue site, tumor purity, cancer type, sequencer identity, or date sequenced. The method performs one or more global batch quality control tests on the batch dataset using at least the cohort-matched reference batch. The method removes respective samples from the batch dataset that fail any one of the one or more global batch quality control tests or flagging for manual inspection respective samples that fail any one of the one or more global batch quality control tests.

57 Claims, 19 Drawing Sheets

Related U.S. Application Data

(60) Provisional application No. 62/943,712, filed on Dec. 4, 2019.

(51) Int. Cl.
*G16B 5/00* (2019.01)
*G16B 50/30* (2019.01)

(56) References Cited

OTHER PUBLICATIONS

Walker et al., Empirical Bayes accomodation of batch-effects in microarray data using identical replicate reference samples: application to RNA expression profiling of blood from Duchenne muscular dystrophy patients, Oct. 2008, BMC Genomics 9: article No. 494, pp. 1-13 (Year: 2008).*

Wang et al., Unifying cancer and normal RNA sequencing data from different sources, Apr. 2018, Scientific Data 5: article No. 180061, pp. 1-8 (Year: 2018).*

Han et al., An Improved Ratio-based (IRB) Batch Effects Removal Algorithm for Cancer Data in a Co-analysis Framework, 2014, 2014 IEEE International Conference on Bioinformatics and Bioengineering, pp. 212-219 (Year: 2014).*

Gibbons et al., Correcting for batch effects in case-control microbiome studies, Apr. 2018, PLoS Computational Biology 14(4): e1006102 (Year: 2018).*

Database Embase, Elsevier Science Publishers, Amsterdam, Aug. 1, 2020, pp. 1-2.

Bell, Joshua SK, et al., "Robust detection of sequencing batch effects in RNA through low-dimensional embedding with subtype-matched reference samples", Tempus, Jun. 24, 2020, 1 page.

Büttner, Maren et al., "A test metric for assessing single-cell RNA-seq batch correction", Nature Methods, Nature Pub. Group, vol. 16, No. 1, Dec. 20, 2018, pp. 43-49.

Espin-Perez et al. Comparison of statistical methods and the use of quality control samples for batch effect correction in human transcriptome data PLoS ONE vol. 13, article e0202947 (Year: 2018).

Finotello, Francesca et al. "Measuring differential gene expression with RNA-seq: challenges and strategies for data analysis", Briefings in Functional Genomics, vol. 14, No. 2, pp. 130-142.

Haghverdi et al. Batch effects in single-cell RNA-sequencing data are corrected by matching mutual nearest neighbors Nature Biotechnology vol. 36, pp. 421-427 (Year: 2018).

Hartley et al. QoRTs: a comprehensive toolset for quality control and data processing of RNA-Seq experiments BMC Bioinformatics vol. 16, article 224 (Year: 2015).

Li, Jun et al. "Normalization, testing, and false discovery rate estimation for RNA-sequencing data", Biostatistics, 2012, 13, 3, pp. 523-538.

Lin, Yong et al. "Comparative studies of de novo assembly tools for next-generation sequencing technologies", Bioinformatics, vol. 27, No. 15, 2011, pp. 2031-2037.

Manimaran, Solaiappan et al. "BatchQC: interactive software for evaluating sample and batch effects in genomic data", Bioinformatics, 32(24) 2016, pp. 3836-3838.

Nyamundanda, Gift et al., "A Novel Statistical Method to Diagnose, Quantify and Correct Batch Effects in Genomic Studies", Scientific Reports, vol. 7, No. 1, Sep. 7, 2017, pp. 1-10.

Polanski, Krzysztof et al., "BBKNN: fast batch alignment of single cell transcriptomes", Bioinformatics, 36(3), Aug. 10, 2019, pp. 964-965.

Robinson, Mark D. et al. "A scaling normalization method for differential expression analysis of RNA-seq data", Genome Biology, 2010, 11:R25, pp. 1-9.

Sheng et al. Multi-perspective quality control of Illumina RNA sequencing data analysis Briefings in Functional Genomics vol. 16, pp. 194-204 (Year: 2017).

Wang et al. BERMUDA: a novel deep transfer learning method for single-cell RNA sequencing batch correction reveals hidden high-resolution cellular subtypes Genome Biology vol. 20, article 165 (Year: 2019).

Komeya, Mitsuru et al. "In vitro spermatogenesis in two-dimensionally spread mouse testis tissues," 2019, Reproductive Medicine and Biology, vol. 18, No. 4, pp. 362-369.

* cited by examiner

Figure 2A:
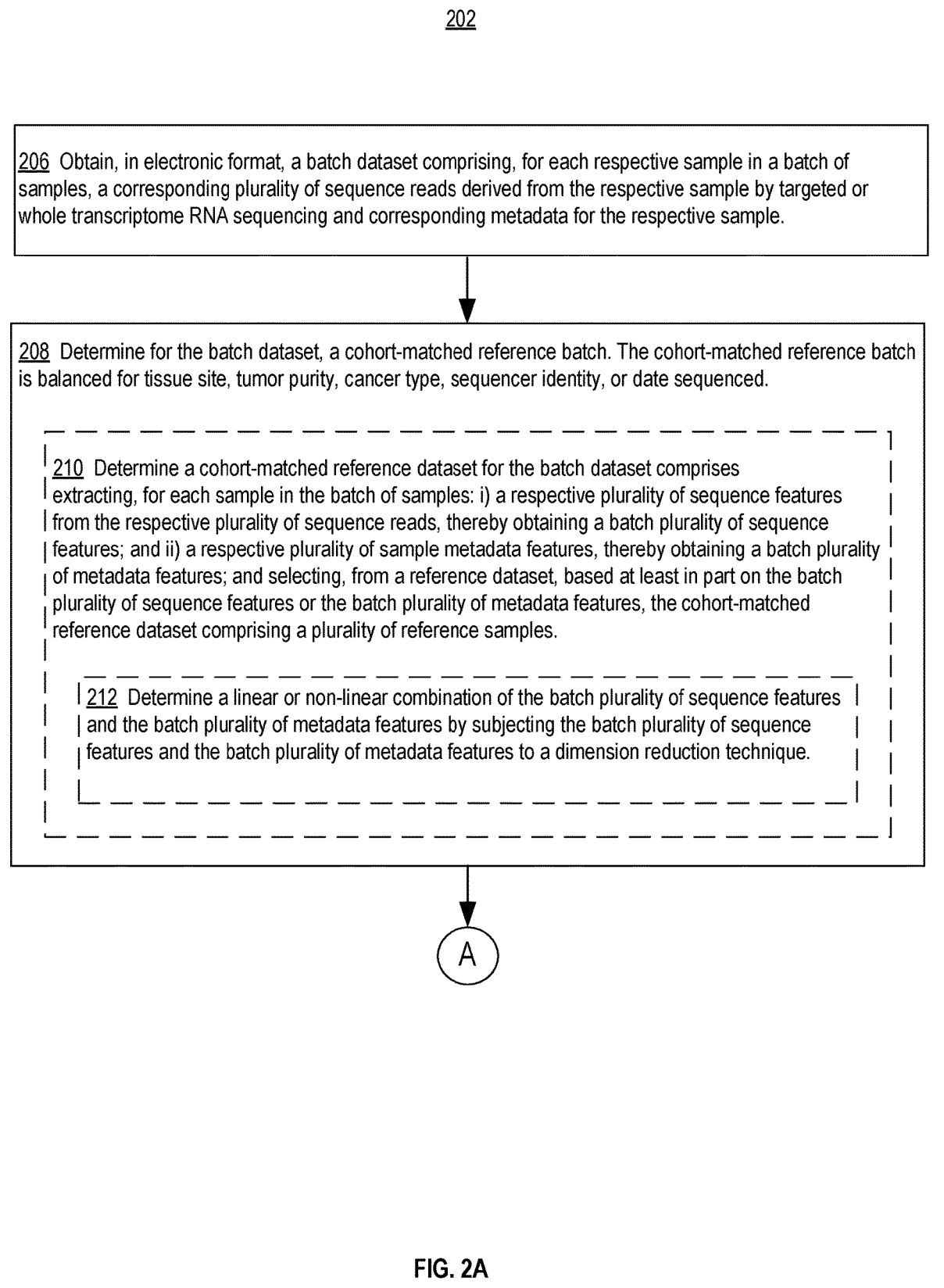

202

206 Obtain, in electronic format, a batch dataset comprising, for each respective sample in a batch of samples, a corresponding plurality of sequence reads derived from the respective sample by targeted or whole transcriptome RNA sequencing and corresponding metadata for the respective sample.

208 Determine for the batch dataset, a cohort-matched reference batch. The cohort-matched reference batch is balanced for tissue site, tumor purity, cancer type, sequencer identity, or date sequenced.

210 Determine a cohort-matched reference dataset for the batch dataset comprises extracting, for each sample in the batch of samples: i) a respective plurality of sequence features from the respective plurality of sequence reads, thereby obtaining a batch plurality of sequence features; and ii) a respective plurality of sample metadata features, thereby obtaining a batch plurality of metadata features; and selecting, from a reference dataset, based at least in part on the batch plurality of sequence features or the batch plurality of metadata features, the cohort-matched reference dataset comprising a plurality of reference samples.

212 Determine a linear or non-linear combination of the batch plurality of sequence features and the batch plurality of metadata features by subjecting the batch plurality of sequence features and the batch plurality of metadata features to a dimension reduction technique.

214 Perform one or more global batch quality control tests on the batch dataset using at least the cohort-matched reference batch.

216 The one or more global batch quality control tests comprise tests for one or more batch effects from a set comprising bioinformatics pipeline analysis, DNA contamination, sample handling, and sequencing methods.

218 Use the cohort-matched reference batch to adjust each sample in the batch dataset for one or more confounding covariates prior to performing the one or more global batch quality control tests.

220 Remove respective samples from the batch dataset that fail any one of the one or more global batch quality control tests or flagging for manual inspection respective samples that fail any one of the one or more global batch quality control tests.

222 Provide, for each sample in the batch of samples, a respective sample report, wherein each respective sample report comprises at least one of a set of expression calls, one or more matched therapies, or one or more matched clinical trials.

230 Perform, for each respective sample in the batch of samples, from the corresponding plurality of sequence reads, one or more single sample quality control tests on the respective sample. Remove respective samples from the batch of samples that fail any one of the one or more single sample quality control tests or flagging for manual inspection respective samples that fail any one of the one or more single sample quality control tests.

240 The one or more global batch quality control tests comprise a first module, and the one or more single sample quality control tests comprise a second module.

FDR Flowcells

0.0 0.2 0.6 0.8 1.0

Number Tested: 521

FDR Pipelines

0.0 0.2 0.6 0.8 1.0

Min: 0.078

Number Tested: 10

SYSTEMS AND METHODS FOR AUTOMATING RNA EXPRESSION CALLS IN A CANCER PREDICTION PIPELINE

CROSS REFERENCE TO RELATED APPLICATIONS

This application is a continuation patent application of U.S. patent application Ser. No. 17/112,877, filed Dec. 4, 2020, which claims priority to U.S. Provisional Patent Application No. 62/943,712, filed on Dec. 4, 2019, the contents of which are hereby incorporated by reference in their entireties for all purposes.

TECHNICAL FIELD

The present disclosure relates generally to using RNA sequence information to perform quality control on batches of RNA sequencing samples.

BACKGROUND

Single sample RNA quality metrics currently implemented in quality control processes in bioinformatics were designed to detect overall sample quality and transcriptome integrity. However, there are many potential sources of error that can affect the quality of samples, and in particular, there are effects that can impact the results of entire batches of sequencing samples. For example, library preparation protocol changes (e.g. reagents, capture probe lot or instrumentation) or changes in the bioinformatics pipeline (e.g. version a program) can result in subtle transcriptome changes, referred to as batch effects, and influence model performance and clinical interpretation of downstream processes (e.g. determining if a gene is over or under-expressed relative to previously sequenced samples, or machine learning models to diagnose tumors of unknown origin). These batch effects are only detectable by leveraging data patterns across samples and require the implementation of new processes between RNA mapping and downstream analysis.

What is needed in the art are improved methods for automatically performing quality control detection and analysis of batch effects of heterogeneous RNA sequencing samples in high throughput.

SUMMARY

Given the background above, improved systems and methods are needed for performing batch quality control (e.g., quality assessment) of RNA samples. Advantageously, the present disclosure provides solutions to these and other shortcomings in the art. For instance, in some embodiments, the systems and methods described herein provide for automated quality control of entire batches of RNA sequencing samples (e.g., thereby performing faster quality control analysis than is currently available). Similarly, in some embodiments, the methods and systems described herein improve diagnostic systems and methods that use RNA expression data, e.g., for precision oncology, by identifying batch effects that would not otherwise be identified through normal single-sample quality control metrics.

One aspect of the present disclosure provides a method of performing quality control. The method is performed at a computer system having one or more processors, and memory storing one or more programs for execution by the one or more processors. The method proceeds by obtaining (a), in electronic form, a batch dataset comprising, for each respective sample in a batch of samples, a corresponding plurality of sequence reads derived from the respective sample by targeted or whole transcriptome RNA sequencing and corresponding metadata for the respective sample. The method continues by determining (b), for the batch dataset, a cohort-matched reference batch, where the cohort-matched reference batch is balanced for tissue site, tumor purity, cancer type, collection method, sequencer identity, and/or date sequenced. The method performs one or more global batch quality control tests on the batch dataset using at least the cohort-matched reference batch. The method removes (d) respective samples from the batch dataset that fail any one of the one or more global batch quality control tests or flagging for manual inspection respective samples that fail any one of the one or more global batch quality control tests.

In some embodiments, determining a cohort-matched reference dataset for the batch dataset comprises extracting, for each sample in the batch of samples: i) a respective plurality of sequence features from the respective plurality of sequence reads, thereby obtaining a batch plurality of sequence features, and ii) a respective plurality of sample metadata features, thereby obtaining a batch plurality of metadata features. In some embodiments, determining the cohort-matched reference dataset further comprises selecting, from a reference dataset, based at least in part on the batch plurality of sample processing and sequence features or the batch plurality of metadata features, the cohort-matched reference dataset comprising a plurality of reference samples.

In some embodiments, the method further comprises performing, for each respective sample in the batch of samples, from the corresponding plurality of sequence reads, one or more single sample quality control tests on the respective sample; and removing respective samples from the batch of samples that fail any one of the one or more single sample quality control tests or flagging for manual inspection respective samples that fail any one of the one or more single sample quality control tests.

In some embodiments, the one or more global batch quality control tests comprises tests for one or more batch effects from a set comprising bioinformatics pipeline analysis and sequencing methods.

In some embodiments, the method further comprises determining a linear or non-linear combination of the batch plurality of sequence features and the batch plurality of metadata features by subjecting the batch plurality of sequence features and the batch plurality of metadata features to a dimension reduction technique.

In some embodiments, the method further comprises using the cohort-matched reference batch to adjust each sample in the batch dataset for one or more confounding covariates prior to performing (c) the one or more global batch quality control tests.

In some embodiments, the method further comprises providing, for each sample in the batch of samples, a respective sample report, where each respective sample report comprises at least one of a set of expression calls, one or more matched therapies, or one or more matched clinical trials.

In some embodiments, the method is performed at a computer system comprising a cloud server. In some embodiments, the one or more global batch quality control tests comprise a first module, and the one or more single sample quality control tests comprise a second module.

Other embodiments are directed to systems, portable consumer devices, and computer readable media associated with the methods described herein. Any embodiment disclosed herein, when applicable, can be applied to any aspect of the methods described herein.

Additional aspects and advantages of the present disclosure will become readily apparent to those skilled in this art from the following detailed description, where only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

FIGS. 2A and 2B collectively provide a flow chart of processes and features for performing quality control on a batch of RNA sequence samples, in which optional blocks are indicated with dashed boxes, in accordance with some embodiments of the present disclosure.

FIGS. 3A, 3B, and 3C collectively show evaluation of technical batch effects on RNA samples collected with PAX or EDTA tubes, in accordance with some embodiments of the present disclosure. FIG. 3A illustrates UMAP embedding of pooled cohort and tissue matched samples. FIGS. 3B and 3C illustrate that Mann Whitney U Test programmatically finds the difference between the matched samples collected with PAX or EDTA tubes in both UMAP coordinates. UMAP coordinates are unordered, and the coordinate that detects the batch effect is arbitrary.

FIG. 4 illustrates UMAP embedding of cohort and tissue matched samples. FIGS. 4B and 4C illustrate the results of a Mann Whitney U Test on each of the UMAP coordinates.

Like reference numerals refer to corresponding parts throughout the several views of the drawings, in accordance with some embodiments of the present disclosure.

DETAILED DESCRIPTION

Figure 1:
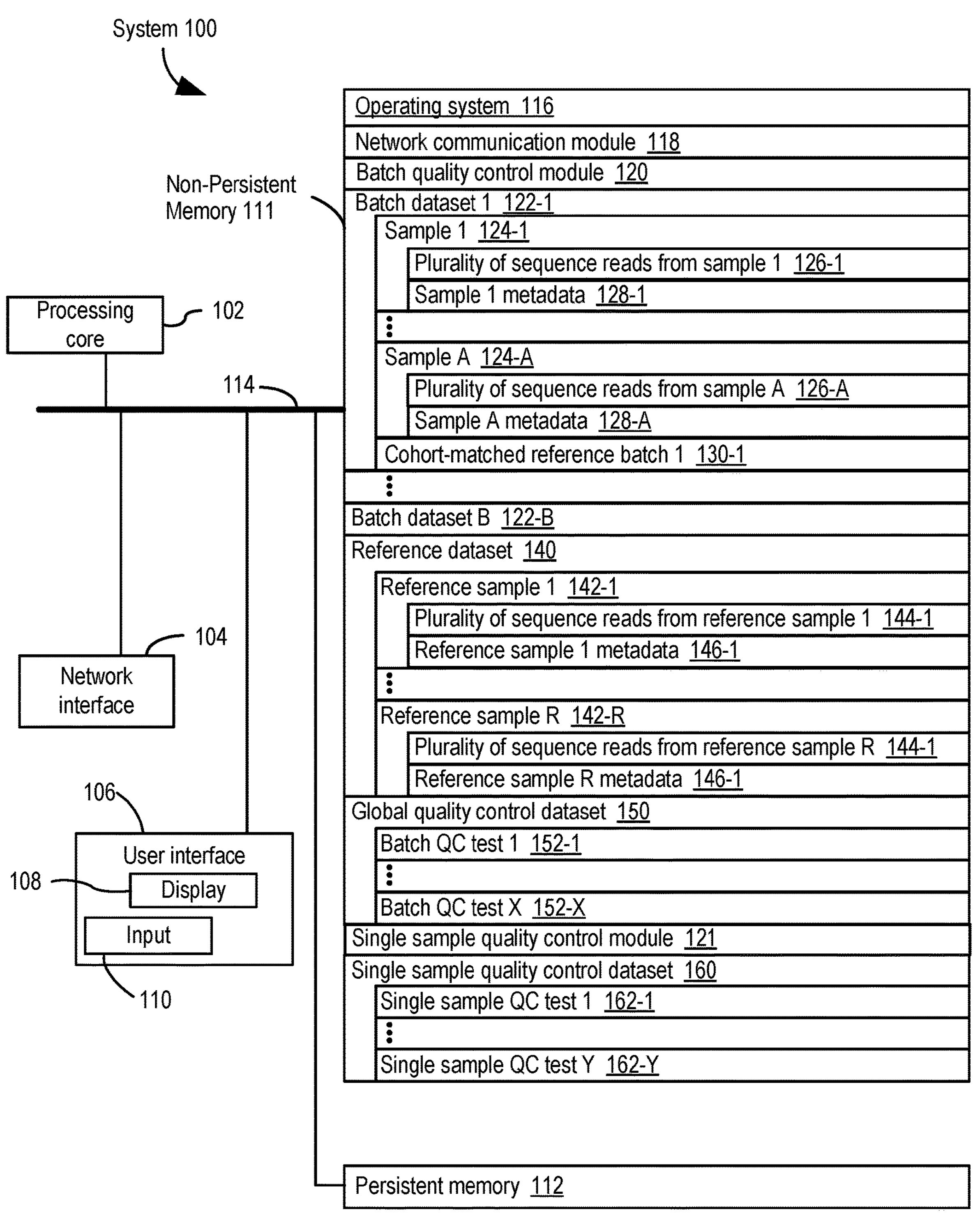
FIG. 1 illustrates a block diagram of an example computing device, in accordance with some embodiments of the present disclosure.

The disclosure herein provides for improved methods of performing quality control analysis of batches (e.g., entire flow cells worth) of RNA sequence samples. The quality control (QC) tests are performed on batches of RNA sequencing samples that include sequencing reads and sample metadata. The methods described herein serve the purpose of ensuring sufficient data quality for performing automated RNA expression call reports and for detecting batch effects that can influence clinical reports. Such methods also serve to ensure the consistency of data quality, which is important for comparing data over time. The quality control methods herein provide for the automatic review and analysis of an entire flow cell of samples.

Benefits

This disclosure provides a novel method that evaluates technical batch effects in a set of transcriptome samples (e.g., a flow cell) by pooling them with a set of validated reference samples matched by cancer type and tissue site (e.g., a cohort-matched reference batch). These methods are improvements over the prior art in that they enable simultaneous global (e.g., performed on the entire set of samples in a batch) and single sample quality control analysis. These quality control methods benefit patients by providing quick and accurate analyses of sample quality, and hence provides for improved and more timely patient diagnosis and treatment.

Laboratories conducting high volumes of RNA sequencing must be extremely wary of technical batch effects if samples are to be compared across extended time periods, which is an imperative for analyses of cancer transcriptomes and determining patient response to treatments. Changes in reagents, protocols, or technologies used in nucleic acid extraction, library preparation, and sequencing can alter transcriptomes in ways that invalidate or complicate comparisons of samples from different batches, necessitating continuous monitoring of sample quality and consistency. This monitoring can be particularly difficult when analyzing samples from distinct tissue sites, as tumor type is the major biological determinant of transcriptome variance in cancer. This means that brain and liver cancer samples, for example, are expected to differ so much transcriptomically that their comparison is not informative for batch effect detection. The fact that the methods herein provide for cohort matching between reference samples and the samples in each individual flow cell makes these quality control metrics more accurate than previous methods.

Definitions

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "comprising," or any variation thereof, when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "including," "includes," "having," "has," "with," or variants thereof are used in either the detailed description and/or the claims, such terms are intended to be inclusive in a manner similar to the term "comprising."

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein.

As used herein, the terms "subject" or "patient" refers to any living or non-living human (e.g., a male human, female human, fetus, pregnant female, child, or the like). In some embodiments, a subject is a male or female of any stage (e.g., a man, a woman or a child).

As used herein, the terms "control," "control sample," "reference," "reference sample," "normal," and "normal sample" describe a sample from a subject that does not have a particular condition, or is otherwise healthy. In an example, a method as disclosed herein can be performed on a subject having a tumor, where the reference sample is a sample taken from a healthy tissue of said subject. In some embodiments, a reference sample can be obtained from the subject (e.g., to serve as a benchmark control for the subject from a particular time). In some embodiments, a reference sample can be obtained from a database. The reference can be, for example, a reference genome that is used to map sequence reads obtained from sequencing a sample from the subject. A reference genome can refer to a haploid or diploid genome to which sequence reads from the biological sample and a constitutional sample can be aligned and compared. An example of constitutional sample can be DNA of white blood cells obtained from the subject. For a haploid genome, there can be only one nucleotide at each locus. For a diploid genome, heterozygous loci can be identified; each heterozygous locus can have two alleles, where either allele can allow a match for alignment to the locus.

As used herein, the term "locus" refers to a position (e.g., a site) within a genome, such as, on a particular chromosome. In some embodiments, a locus refers to a single nucleotide position within a genome, such as, on a particular chromosome. In some embodiments, a locus refers to a small group of nucleotide positions within a genome, for example, as defined by a mutation (e.g., substitution, insertion, or deletion) of consecutive nucleotides within a cancer genome. Because normal mammalian cells have diploid genomes, a normal mammalian genome (e.g., a human genome) will generally have two copies of every locus in the genome, or at least two copies of every locus located on the autosomal chromosomes, for example, one copy on the maternal autosomal chromosome and one copy on the paternal autosomal chromosome.

As used herein, the term "allele" refers to a particular sequence of one or more nucleotides at a chromosomal locus.

As used herein, the term "reference allele" refers to the sequence of one or more nucleotides at a chromosomal locus that is either the predominant allele represented at that chromosomal locus within the population of the species (e.g., the "wild-type" sequence), or an allele that is predefined within a reference genome for the species.

As used herein, the term "variant allele" refers to a sequence of one or more nucleotides at a chromosomal locus that is either not the predominant allele represented at that chromosomal locus within the population of the species (e.g., not the "wild-type" sequence), or not an allele that is predefined within a reference genome for the species.

As used herein, the terms "single nucleotide variant," "SNV," "single nucleotide polymorphism," or "SNP" refer to a substitution of one nucleotide to a different nucleotide at a position (e.g., site) of a nucleotide sequence, for example, a sequence read from an individual. A substitution from a first nucleobase X to a second nucleobase Y may be denoted as "X>Y." For example, a cytosine to thymine SNP may be denoted as "C>T." The term "het-SNP" refers to a heterozygous SNP, where the genome is at least diploid and at least one—but not all—of the two or more homologous sequences exhibits the particular SNP. Similarly, a "hom-SNP" is a homologous SNP, where each homologous sequence of a polyploid genome has the same variant compared to the reference genome. As used herein, the term "structural variant" or "SV" refers to large (e.g., larger than 1 kb) regions of a genome that have undergone physical transformations such as inversions, insertions, deletions, or duplications (e.g., see review of human genome SVs by Spielmann et al., 2018, Nat Rev Genetics 19:453-467).

As used herein, the term "indel" refers to insertion and/or deletion events of stretches of one or more nucleotides, either within a single gene locus or across multiple genes.

As used herein, the term "copy number variant," "CNV," or "copy number variation" refers to regions of a genome that are repeated. These may be categorized as short or long repeats, in regards to the number of nucleotides that are repeated over the genome regions. Long repeats typically refer to cases where entire genes, or large portions of a gene, are repeated one or more times.

As used herein, the term "mutation," refers to a detectable change in the genetic material of one or more cells. In a particular example, one or more mutations can be found in, and can identify, cancer cells (e.g., driver and passenger mutations). A mutation can be transmitted from a parent cell to a daughter cell. A person having skill in the art will appreciate that a genetic mutation (e.g., a driver mutation) in a parent cell can induce additional, different mutations (e.g., passenger mutations) in a daughter cell. A mutation generally occurs in a nucleic acid. In a particular example, a mutation can be a detectable change in one or more deoxyribonucleic acids or fragments thereof. A mutation generally refers to nucleotides that are added, deleted, substituted for, inverted, or transposed to a new position in a nucleic acid. A mutation can be a spontaneous mutation or an experimentally induced mutation. A mutation in the sequence of a particular tissue is an example of a "tissue-specific allele." For example, a tumor can have a mutation that results in an allele at a locus that does not occur in normal cells. Another example of a "tissue-specific allele" is a fetal-specific allele that occurs in the fetal tissue, but not the maternal tissue.

As used herein, the term "genomic variant" may refer to one or more mutations, copy number variants, indels, single nucleotide variants, or variant alleles. A genomic variant may also refer to a combination of one or more above.

As used herein the term "cancer," "cancerous tissue," or "tumor" refers to an abnormal mass of tissue in which the growth of the mass surpasses and is not coordinated with the growth of normal tissue. In the case of hematological cancers, this includes a volume of blood or other bodily fluid containing cancerous cells. A cancer or tumor can be defined as "benign" or "malignant" depending on the following characteristics: degree of cellular differentiation including morphology and functionality, rate of growth, local invasion and metastasis. A "benign" tumor can be well differentiated, have characteristically slower growth than a malignant tumor and remain localized to the site of origin. In addition, in some cases a benign tumor does not have the capacity to infiltrate, invade or metastasize to distant sites. A "malignant" tumor can be a poorly differentiated (anaplasia), have characteristically rapid growth accompanied by progressive infiltration, invasion, and destruction of the surrounding tissue. Furthermore, a malignant tumor can have the capacity to metastasize to distant sites. Accordingly, a cancer cell is a cell found within the abnormal mass of tissue whose growth is not coordinated with the growth of normal tissue. Accordingly, a "tumor sample" or "somatic biopsy" refers to a biological sample obtained or derived from a tumor of a subject, as described herein.

As used herein, the term "somatic biopsy" refers to a biopsy of a subject. In some embodiments, the biopsy is of solid tissue. In some embodiments, it is a liquid biopsy.

As used herein, the terms "sequencing," "sequence determination," and the like as used herein refers generally to any and all biochemical processes that may be used to determine the order of biological macromolecules such as nucleic acids or proteins. For example, sequencing data can include all or a portion of the nucleotide bases in a nucleic acid molecule such as an mRNA transcript or a genomic locus.

As used herein, the term "sequence reads" or "reads" refers to nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads). The length of the sequence read is often associated with the particular sequencing technology. High-throughput methods, for example, provide sequence reads that can vary in size from tens to hundreds of base pairs (bp). In some embodiments, the sequence reads are of a mean, median or average length of about 15 bp to 900 bp long (e.g., about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median, or average length of about 1000 bp, 2000 bp, 5000 bp, 10,000 bp, or 50,000 bp or more. Nanopore sequencing, for example, can provide sequence reads that can vary in size from tens to hundreds to thousands of base pairs. Illumina parallel sequencing can provide sequence reads that do not vary as much, for example, most of the sequence reads can be smaller than 200 bp. A sequence read (or sequencing read) can refer to sequence information corresponding to a nucleic acid molecule (e.g., a string of nucleotides). For example, a sequence read can correspond to a string of nucleotides (e.g., about 20 to about 150) from part of a nucleic acid fragment, can correspond to a string of nucleotides at one or both ends of a nucleic acid fragment, or can correspond to nucleotides of the entire nucleic acid fragment. A sequence read can be obtained in a variety of ways, for example, using sequencing techniques or using probes, for example, in hybridization arrays or capture probes, or amplification techniques, such as the polymerase chain reaction (PCR) or linear amplification using a single primer or isothermal amplification.

As used herein, the term "read segment" or "read" refers to any nucleotide sequences including sequence reads obtained from an individual and/or nucleotide sequences derived from the initial sequence read from a sample obtained from an individual. For example, a read segment can refer to an aligned sequence read, a collapsed sequence read, or a stitched read. Furthermore, a read segment can refer to an individual nucleotide base, such as a single nucleotide variant.

As used herein, the term "read-depth," "sequencing depth," or "depth" refers to a total number of read segments from a sample obtained from an individual at a given position, region, or locus. The locus can be as small as a nucleotide, or as large as a chromosome arm, or as large as an entire genome. Sequencing depth can be expressed as "Yx," for example, 50×, 100×, etc., where "Y" refers to the number of times a locus is covered with a sequence read. In some embodiments, the depth refers to the average sequencing depth across the genome, across the exome, across the transcriptome, or across a targeted sequencing panel. Sequencing depth can also be applied to multiple loci, the whole genome, in which case Y can refer to the mean number of times a loci or a haploid genome, a whole genome, a whole transcriptome, or a whole exome, respectively, is sequenced. When a mean depth is quoted, the actual depth for different loci included in the dataset can span over a range of values. Ultra-deep sequencing can refer to at least 100× in sequencing depth at a locus.

As used herein the term "sequencing breadth" refers to what fraction of a particular reference transcriptome (e.g., human reference exome), a particular reference genome (e.g., human reference genome), or part of the transcriptome or genome has been analyzed. The denominator of the fraction can be a repeat-masked genome, and thus 100% can correspond to all of the reference genome minus the masked parts. A repeat-masked transcriptome or genome can refer to a transcriptome or genome in which sequence repeats are masked (e.g., sequence reads align to unmasked portions of the transcriptome or genome). Any parts of a transcriptome or genome can be masked, and thus one can focus on any particular part of a reference exome or genome. Broad sequencing can refer to sequencing and analyzing at least 0.1% of the reference transcriptome or genome.

As used herein, the term "reference transcriptome" refers to any particular known, sequenced, or characterized transcriptome, whether partial or complete, of any tissue from any organism or pathogen that may be used to reference identified sequences from a subject. Exemplary reference transcriptomes used for human subjects are provided in the online MiTranscriptome database described by Iyer et al 2015 The landscape of long noncoding RNAs in the human transcriptome. Nat Genet 47, 199-208, the CHESS database that is described by Pertea et al. 2018 CHESS: a new human gene catalog curated from thousands of large-scale RNA sequencing experiments reveals extensive transcriptional noise. Gen Biol 19:208, and in the online ENCODE database hosted by the ENCODE project.

As used herein, the term "expression call" refers to an RNA expression differential call (e.g., a determination of whether a particular sample from a subject exhibits a higher or lower expression for a particular RNA in comparison to a reference transcriptome). In some embodiments, an expression call is based at least in part on gene abundance counts.

As used herein, the term "reference exome" refers to any particular known, sequenced, or characterized exome, whether partial or complete, of any tissue from any organism or pathogen that may be used to reference identified sequences from a subject. Exemplary reference exomes used for human subjects, as well as many other organisms, are provided in the online GENCODE database hosted by the GENCODE consortium, for instance Release 29 (GRCh38.p12) of the human exome assembly.

As used herein, the term "reference genome" refers to any particular known, sequenced, or characterized genome, whether partial or complete, of any organism or pathogen that may be used to reference identified sequences from a subject. Exemplary reference genomes used for human subjects as well as many other organisms are provided in the on-line genome browser hosted by the National Center for Biotechnology Information ("NCBI") or the University of California, Santa Cruz (UCSC). A "genome" refers to the complete genetic information of an organism or pathogen, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes or genetic sequences. In some embodiments, a reference genome includes sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38).

As used herein, the term "assay" refers to a technique for determining a property of a substance, for example, a nucleic acid, a protein, a cell, a tissue, or an organ. An assay (e.g., a first assay or a second assay) can comprise a technique for determining the copy number variation of nucleic acids in a sample, the methylation status of nucleic acids in a sample, the fragment size distribution of nucleic acids in a sample, the mutational status of nucleic acids in a sample, or the fragmentation pattern of nucleic acids in a sample. Any assay known to a person having ordinary skill in the art can be used to detect any of the properties of nucleic acids mentioned herein. Properties of nucleic acids can include a sequence, genomic identity, copy number, methylation state at one or more nucleotide positions, size of the nucleic acid, presence or absence of a mutation in the nucleic acid at one or more nucleotide positions, and pattern of fragmentation of a nucleic acid (e.g., the nucleotide position(s) at which a nucleic acid fragments). An assay or method can have a particular sensitivity and/or specificity, and their relative usefulness as a diagnostic tool can be measured using ROC-AUC statistics.

As used herein, the term "relative abundance" can refer to a ratio of a first amount of nucleic acid fragments having a particular characteristic (e.g., aligning to a particular region of the exome) to a second amount of nucleic acid fragments having a particular characteristic (e.g., aligning to a particular region of the exome). In one example, relative abundance may refer to a ratio of the number of mRNA transcripts encoding a particular gene in a sample (e.g., aligning to a particular region of the exome) to the total number of mRNA transcripts in the sample.

As used herein, two datasets are "balanced" with respect to a characteristic when the percentage of the number samples having each type of characteristic in the two datasets is within a set percentage of each other. Unless otherwise specified, two data sets are balanced with respect to a characteristic when the percentage of the number samples having each type of characteristic in the two datasets is within 10%. For instance, if, in a batch data set, 15% of the samples are lung cancer samples, 25% of the samples are brain cancer samples, and 60% of the samples are colon cancer samples, a reference dataset is considered to be balanced to the batch dataset if, in the reference data set, from 5%-25% of the samples are lung cancer samples, 15%-35% of the samples are brain cancer samples, and 50%-70% of the samples are colon cancer samples. In some embodiments, two datasets are balanced with respect to a characteristic when the percentage of the number samples having each type of characteristic in the two datasets is within 1%, within 2%, within 3%, within 4%, within 5%, within 6%, within 7%, within 8%, within 9%, within 10%, within 11%, within 12%, within 13%, within 14%, within 15%, within 16%, within 17%, within 18%, within 19%, within 20%, within 21%, within 22%, within 23%, within 24%, or within 25% of each other. Generally, the balancing of a first feature and the balancing of a second feature are considered independently of one another. However, in some embodiments, the balancing of a first feature and the balancing of a second feature are considered together. That is, in some embodiments, it a composite of at least two characteristics that is balanced. For example, the percentage of brain cancer samples taken from a skin tissue and the percentage of brain cancer samples taken from a lung tissue in a batch dataset are balanced to the percentage of brain cancer samples taken from a skin tissue and the percentage of brain cancer samples taken from a lung tissue in a reference dataset, as opposed to just balancing the percentage of brain cancer samples, samples taken from skin tissue, and samples taken from lung tissue. In some embodiments, a rare characteristic in a batch dataset will not be balanced in the reference dataset, e.g., because of the unavailability of a sufficient number of reference samples that share the rare characteristic.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

Example System Embodiments

Now that an overview of some aspects of the present disclosure and some definitions used in the present disclosure has been provided, details of an exemplary system are described in conjunction with FIG. 1. FIG. 1 is a block diagram illustrating a system 100 in accordance with some implementations. The system 100 in some implementations includes one or more processing units CPU(s) 102 (also referred to as processors), one or more network interfaces 104, a user interface 106 including (optionally) a display 108 and an input system 110, a non-persistent memory 111, a persistent memory 112, and one or more communication buses 114 for interconnecting these components. The one or more communication buses 114 optionally include circuitry (sometimes called a chipset) that interconnects and controls communications between system components. The non-persistent memory 111 typically includes high-speed random access memory, such as DRAM, SRAM, DDR RAM, ROM, EEPROM, flash memory, whereas the persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 112 optionally includes one or more storage devices remotely located from the CPU(s) 102. The persistent memory 112, and the non-volatile memory device(s) within the non-persistent memory 112, comprise non-transitory computer readable storage medium. In some implementations, the non-persistent memory 111 or alternatively the non-transitory computer readable storage medium stores the following programs, modules and data structures, or a subset thereof, sometimes in conjunction with the persistent memory 112:

- an optional operating system 116, which includes procedures for handling various basic system services and for performing hardware dependent tasks;
- an optional network communication module (or instructions) 118 for connecting the system 100 with other devices and/or a communication network 104;
- a batch quality control module 120 for performing batch quality control of batches of RNA sequencing samples;
- one or more batch datasets 122, where each batch dataset includes, for each sample 124 in a plurality (e.g., a batch) of samples, at least a corresponding plurality of sequence reads 126 and corresponding sample metadata 128, also included in each batch dataset is a corresponding cohort-matched reference batch 130;
- a reference sample dataset 140 storing one or more references samples 142, where each reference sample includes at least a corresponding plurality of reference sample sequences 144 and corresponding reference sample metadata 146;
- a global quality control dataset 150 for storing one or more batch quality control tests 152, where the one or more batch quality control tests 152 are performed, via the quality control module 120, on the plurality of samples (e.g., 124-1, . . . 124-A) included in a batch datasets (e.g., batch dataset 122-1);
- a single sample quality control module 121 for performing single sample quality control of RNA sequencing samples; and
- a single sample quality control dataset 160 for storing one or more single sample quality control tests 162, where the one or more single sample quality control tests 162 are performed, via the quality control module 120, on individual samples 124 included in a batch dataset 122.

In various implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 111 optionally stores a subset of the modules and data structures identified above. Furthermore, in some embodiments, the memory stores additional modules and data structures not described above. In some embodiments, one or more of the above identified elements is stored in a computer system, other than that of visualization system 100, that is addressable by visualization system 100 so that visualization system 100 may retrieve all or a portion of such data when needed.

Although FIG. 1 depicts a "system 100," the figure is intended more as a functional description of the various features that may be present in computer systems than as a structural schematic of the implementations described herein. In practice, and as recognized by those of ordinary skill in the art, items shown separately could be combined and some items could be separated. Moreover, although FIG. 1 depicts certain data and modules in non-persistent memory 111, some or all of these data and modules instead may be stored in persistent memory 112 or in more than one memory. For example, in some embodiments, at least one batch dataset 122 is stored in a remote storage device, which can be a part of a cloud-based infrastructure. In some embodiments, at least dataset one batch dataset 122 is stored on a cloud-based infrastructure. In some embodiments, batch dataset 122, batch quality control module 120, single sample quality control module 121, reference dataset 140, global QC dataset 150, and/or single sample QC dataset 160 can also be stored in the remote storage device(s). In some embodiments, other configurations of data and module storage are employed.

Analysis of Batches and Samples

Now that details of a system 100 in accordance with the present disclosure, have been disclosed, details regarding processes and features of the system, in accordance with various embodiments of the present disclosure, are disclosed below. Specifically, example processes are described below with reference to FIGS. 2A, 2B, 15, 16, and 17. In some embodiments, such processes and features of the system are carried out by modules 118, 120, and/or 121, as illustrated in FIG. 1.

Block 202.

Referring to block 202 of FIG. 2A, the method performs quality control. In some embodiments, the quality control is performed on a single batch dataset (e.g., comprising a single flow cell of RNA samples). In some embodiments, the quality control is performed simultaneously on two or more batch datasets (e.g., two or more flow cells of RNA samples, where each flow cell is analyzed on either a same day or a different day). In some embodiments, the quality control is performed simultaneously on a plurality of batch datasets (e.g., on a plurality of flow cells).

Referring to block 204, in some embodiments, the methods described herein are performed at a computer system comprising a cloud server. That is, in some embodiments, the methods described herein can be performed either wholly or in part on remote systems. For example, as described above, in some embodiments, one or more of the datasets are stored locally, and at least one of the batch quality control module 120 and/or the single sample quality control module 121 are stored on a cloud server (e.g., in the cloud). In some embodiments, reference dataset 140, global quality control dataset 150, and/or single sample quality control dataset 160 are also stored on a cloud server. In some embodiments, necessary data (e.g., one or more batch datasets 122) can be transmitted between local and cloud servers.

Obtain Initial Batch Dataset 122 Information

Block 206.

Referring to block 206 of FIG. 2A, a batch dataset is obtained in electronic format (e.g., information for each sample in the batch dataset is stored in a .csv file). The batch dataset comprises, for each respective sample in a plurality (e.g., batch) of samples, a corresponding plurality of sequence reads derived from the respective sample by targeted panel or whole transcriptome sequencing. In some embodiments, each corresponding plurality of sequence reads is obtained from a plurality of RNA molecules or derivatives of said plurality of RNA molecules (e.g., derivatives such as cDNA). In some embodiments, each corresponding plurality of sequence reads is obtained by full transcriptome sequencing. In some embodiments, one or more corresponding pluralities of sequence reads are derived from RNA that has been isolated from a solid or hematological tumor (e.g., a solid biopsy). In some embodiments, one or more corresponding pluralities of sequence reads are derived from germline samples obtained from the respective subjects.

In some embodiments, one or more corresponding pluralities of sequence reads are generated by next-generation sequencing. In some embodiments, one or more corresponding pluralities of sequence reads are generated from short-read paired end next-generation sequencing. In some embodiments, one or more corresponding pluralities of sequence reads are generated from short-read next-generation sequencing with one or more spike-in controls. In some embodiments, the one or more spike-in controls calibrate variation in sequence reads across a population of cells (e.g., the volume of RNA reads obtained from each cell can vary significantly and spiking helps to normalize reads across a set of cells). In some embodiments, one or more corresponding pluralities of sequence reads are obtained by targeted panel sequencing using a plurality of probes.

Methods for mRNA sequencing are well known in the art. In some embodiments, the mRNA is reverse transcribed to cDNA prior to sequencing. For example, methods of RNA-seq for use in accordance with block 210 are disclosed in Nagalakshmi et al., 2008, Science 320, 1344-1349; and Finotell and Camillo, 2014, *Briefings in Functional Genomics* 14(2), 130-142, each of which is hereby incorporated by reference. In some embodiments, the mRNA sequencing is performed by whole exome sequencing (WES). In some embodiments, WES is performed by isolating RNA from a tissue sample, generating a cDNA library, optionally selecting for desired sequences and/or depleting unwanted RNA molecules, and then sequencing the cDNA library, for example, using next-generation sequencing techniques. For a review of the use of whole exome sequencing techniques in cancer diagnosis, see, Serrati et al., 2016, Onco Targets Ther. 9, 7355-7365 and Cieslik, M. et al. 2015 *Genome Res.* 25, 1372-81, the content of each of which is hereby incorporated herein by reference in its entirety, for all purposes. In some embodiments, the mRNA sequencing is performed by nanopore sequencing. A review of the use of nanopore sequencing techniques on the human genome can be found in Jain et al., 2018, Nature 36(4), 338-345. This list is not exhaustive of the RNA sequencing methods that may be used in accordance with the methods described herein. In some embodiments, the RNA sequencing is performed according to one or more sequencing methods known in the art. See e.g., a review of RNA sequencing methods Kukurba et al. 2015 *Cold Spring Harb Protoc.* 11:951-969.

Methods of next-generation sequencing for use in accordance with methods described herein are disclosed in Shendure 2008 *Nat. Biotechnology* 26:1135-1145 and Fullwood et al. 2009 *Genome Res.* 19:521-532, which are each hereby incorporated by reference. Next generation sequencing methods well known in the art include synthesis technology (Illumina), pyrosequencing (454 Life Sciences), ion semiconductor technology (Ion Torrent sequencing), single-molecule real-time sequencing (Pacific Biosciences), sequencing by ligation (SOLID sequencing), nanopore sequencing (Oxford Nanopore Technologies), or paired-end sequencing. In some embodiments, massively parallel sequencing is performed using sequencing-by-synthesis with reversible dye terminators.

RNA-seq is a methodology for RNA profiling based on next-generation sequencing that enables the measurement and comparison of gene expression patterns across a plurality of subjects. In some embodiments, millions of short strings, called 'sequence reads,' are generated from sequencing random positions of cDNA prepared from the input RNAs that are obtained from tumor tissue of a subject. In some embodiments, RNA-seq gene expression data was generated from formalin fixed paraffin embedded tumor samples using an exome-capture based RNA-seq protocol. These reads can then be computationally mapped on a reference genome to reveal a 'transcriptional map,' where the number of sequence reads aligned to each gene gives a measure of its level of expression (e.g., abundance). In some embodiments, the RNA-seq expression levels (e.g., raw read counts) are normalized (e.g., to correct for GC content, sequencing depth, and/or gene length). In some embodiments, methods of mapping raw RNA sequence reads to the transcriptome, quantifying gene counts, and normalization are performed as described in U.S. Patent Application No. 62/735,349, entitled "Methods of Normalizing and Correcting RNA Expression Data," filed on Sep. 24, 2018.

In some alternative embodiments, rather than using RNA-seq, microarrays are used to examine RNA profiling. Such microarrays are disclosed in Wang et al., 2009, *Nat Rev Genet* 10, 57-63; Roy et al., 2011, *Brief Funct Genomic* 10:135-150; Shendure, 2008 *Nat Methods* 5, 585-587; Cloonan et al., 2008, "Stem cell transcriptome profiling via massive-scale mRNA sequencing," Nat. Methods 5, 613-619; Mortazavi et al., 2008, "Mapping and quantifying mammalian transcriptomes by RNA-Seq," Nat Methods 5, 621-628; and Bullard et al., 2010, "Evaluation of statistical methods for normalization and differential expression in mRNA-Seq experiments" BMC Bioinformatics 11, p. 94, each of which is hereby incorporated by reference.

The first computational step of the RNA-seq data analysis pipeline is read mapping: reads are aligned to a reference genome or transcriptome by identifying gene regions that match read sequences. Any of a variety of alignment tools can be used for this task. See, for example, Hatem et al., 2013 *BMC Bioinformatics* 14, 184; and Engstrom et al. 2013 *Nat Methods* 10, 1185-1191, each of which is hereby incorporated by reference. In some embodiments, the mapping process starts by building an index of either the reference genome or the reads, which is then used to retrieve the set of positions in the reference sequence where the reads are more likely to align. Once this subset of possible mapping locations has been identified, alignment is performed in these candidate regions with slower and more sensitive algorithms. See, for example, Flicek and Birney, 2009, *Nat Methods* 6(Suppl. 11), S6-S12, which is hereby incorporated by reference. In some embodiments, the mapping tool is a methodology that makes use of pseudoalignment (e.g., alignment of read sequences to transcripts but not to genomic locations). See, for example, Bray et al. 2016 Near-optimal probabilistic RNA-seq quantification. Nat Biotech 34, 525-527, which is hereby incorporated by reference.

After mapping, the reads aligned to each coding unit, such as exon, transcript, or gene, are used to compute read counts, in order to provide an estimate of its abundance (e.g., expression) level. In some embodiments, such counting considers the total number of reads overlapping the exons of a gene. However, because in some instances some of the sequence reads map outside the boundaries of known exons, alternative embodiments consider the whole length of a gene, also counting reads from introns. Further still, in some embodiments spliced reads are used to model the abundance of different splicing isoforms of a gene. See, for example, Trapnell et al., 2010 Nat Biotechnol 28, 511-515; and Gatto et al, 2014 Nucleic Acids Res 42, p. e71, each of which is hereby incorporated by reference.

As explained above, quantification of transcript abundance from RNA-seq data is typically implemented in the analysis pipeline through two computational steps: alignment of reads to a reference genome or transcriptome, and subsequent estimation of transcript and isoform abundances based on aligned reads. Unfortunately, the reads generated by the most used RNA-Seq technologies are generally much shorter than the transcripts from which they are sampled. Consequently, in the presence of transcripts with similar sequences, it is not always possible to uniquely assign short sequence reads to a specific gene. Such sequence reads are referred to as "multireads" because they are homologous to more than one region of the reference genome or homologous to multiple transcripts in the reference transcriptome. In some embodiments, such multireads are discarded, that is, they do not contribute to gene abundance counts. In some embodiments, programs such as MMSEQ or RSEM are used to resolve the ambiguity. See examples of methodologies used to resolve multireads in Turro et al., 2011 Genome Biol 12, p. R13; and Nicolae et al., Algorithms Mol Biol 6, 9, each of which is hereby incorporated by reference.

Another aspect of RNA-seq is normalization of sequence read counts. In some embodiments, this includes normalization to take into account different sequencing depths. See, for example, Lin et al., 2011 Bioinformatics 27, 2031-2037; Robinson Oshlack, 2010 Genome Biol 11, R25; and Li et al., 2012 Biostatistics 13, 523-538, each of which is hereby incorporated by reference. In some embodiments, sequence read counts are normalized to account for gene length bias. See, Finotell and Camillo, 2014 Briefings in Functional Genomics 14(2), 130-142, which is hereby incorporated by reference.

In embodiments where one or more corresponding pluralities of sequence reads are generated from targeted panel sequencing using a plurality of probes, each respective probe in the plurality of probes uniquely represents a different portion of a reference genome. In such embodiments, each sequence read in the corresponding plurality of sequence reads corresponds to at least one probe in the plurality of probes.

Each respective probe in the plurality of probes uniquely targets a different (e.g., a respective) portion of a reference transcriptome (e.g., of the human reference transcriptome). Each sequence read in the second plurality of sequence reads and each sequence reads in the third plurality of sequence reads corresponds to least one probe in the plurality of probes. In some embodiments, whole genome sequencing is used, for example, instead of targeted panel sequencing.

In some embodiments, the second plurality of sequence reads has an average depth of at least 50× across the plurality of probes. In some embodiments, the second plurality of sequence reads has an average depth of at least 400× across the plurality of probes. In other embodiments, the second plurality of sequence reads has an average depth of at least 10×, 15×, 20×, 25×, 30×, 40×, 50×, 75×, 100×, 150×, 200×, 250×, 300×, 400×, 500×, or greater.

In some embodiments, the plurality of probes includes probes for at least three hundred different genes. In some embodiments, the plurality of probes includes probes for at least five hundred different genes. In yet other embodiments, the plurality of probes includes at least 50, 100, 150, 200, 250, 300, 400, 500, 600, 700, 800, 900, 1000, 1500, 2000, 3000, 4000, 5000, or more different genes.

Block 208.

Referring to block 208 of FIG. 2A, a cohort-matched reference batch is determined for the batch dataset. The cohort-matched reference batch is balanced for tissue site, tumor purity, cancer type, sequencer identity, or data sequenced. In some embodiments, a size of (e.g., the number of samples in) the cohort-matched reference batch is the same as a size of the batch dataset. In some embodiments, the cohort-matched reference batch is of a different size than the batch dataset.

Determine a Cohort-Matched Reference Dataset 130 from Reference Dataset 140

Referring to block 210 of FIG. 2A, in some embodiments, determining a cohort-matched reference dataset for the batch dataset comprises extracting, for each sample in the batch of samples: i) a respective plurality of sequence features from the respective plurality of sequence reads, thereby obtaining a batch plurality of sequence features, and ii) a respective plurality of sample metadata features, thereby obtaining a batch plurality of metadata features. In some embodiments, selecting, from a reference dataset, based at least in part on the batch plurality of sequence features or the batch plurality of metadata features, the cohort-matched reference dataset comprising a plurality of reference samples.

In some embodiments, the cohort-matched reference dataset comprises a plurality of reference samples. In some embodiments, each reference sample in the plurality of reference samples comprises a corresponding plurality of sequence reads derived from the respective reference sample by targeted or whole transcriptome RNA sequencing and corresponding metadata for the respective reference sample. In some embodiments, reference samples for a cohort-matched reference datasets are selected based at least in part on sample characteristics from sample metadata such as RNA transcription profiles (e.g., as determined from a plurality of sequence reads), clinical data (e.g., patient diagnosis, treatment outcomes, etc.), gender, biopsy type (e.g., heme vs. solid biopsy), and/or molecular data (e.g., genomic mutations).

In some embodiments, patient diagnosis comprises cancer type and/or cancer stage. In some embodiments, a respective cancer type for each sample in the batch dataset is selected from the set consisting of a tumor of a predetermined stage of a brain cancer, a predetermined stage of a glioblastoma, a predetermined stage of a prostate cancer, a predetermined stage of a pancreatic cancer, a predetermined stage of a kidney cancer, a predetermined stage of a colorectal cancer, a predetermined stage of an ovarian cancer, a predetermined stage of an endometrial cancer, or a predetermined stage of a breast cancer.

In some embodiments, the biopsy type comprises a somatic biopsy. In some embodiments, a somatic biopsy comprises macrodissected formalin fixed paraffin embedded (FFPE) tissue sections, surgical biopsy, skin biopsy, punch biopsy, prostate biopsy, bone biopsy, bone marrow biopsy, needle biopsy, CT-guided biopsy, ultrasound-guided biopsy, fine needle aspiration, aspiration biopsy, fresh tissue or blood samples. In some embodiments, the somatic biopsy is of a breast tumor, a glioblastoma, a prostate tumor, a pancreatic tumor, a kidney tumor, a colorectal tumor, an ovarian tumor, an endometrial tumor, a breast tumor, or a combination thereof. Biopsies are typically performed after one or more less-invasive clinical tests suggest that a patient has or has a likelihood of having one or more tumors. The type of biopsy often depends on the location of the tumor. For example, biopsies of kidney tumors are frequently performed endoscopically, while biopsies of ovarian tumors frequently comprise tissue scraping.

In some embodiments, genomic mutations comprise copy number variants, somatic mutations, germline mutations, microsatellite instability indications, tumor mutational burden, indications of pathogen load, or tumor cellularity.

Examples of copy number variations are described in Shilien and Malkin 2009 Genome Med 1, 62. Microsatellite instability indications can be determined as described by Buhard et al. 2006 J Clinical Onco 24(2), 241. Examples of the determination of tumor mutational burden are described in Chalmers et al 2017 Genome Med 9, 34. Indications of pathogen load and/or the indication of immune infiltration may be determined as described, for example, by Barber et al 2015 PLOS Pathog 11(1): e1004558 and Pages et al 2010 Oncogene 29, 1093-1102. In some cases, an indication of tumor cellularity is determined from a somatic biopsy by comparing a number of cancerous cells with a number of normal cells obtained in the somatic biopsy. In some cases, an indication of tumor cellularity is determined from one or more images of a somatic biopsy (e.g., by counting and identifying cancer vs. non-cancer cells).

Cohort-matched reference datasets are, in some embodiments, balanced to correspond as closely as possible to the sample types present in the batch dataset (e.g., by selecting reference samples that are similar to respective samples in the plurality of samples in the batch dataset). In some embodiments, similarity between reference samples and batch dataset samples is determined based on at least one of the sample characteristics that are described above. In some embodiments, a cohort-matched reference batch is selected from the reference database to include as many reference samples as possible (e.g., so as to maintain a reference batch that is balanced for tissue site, tumor purity, cancer type, sequencer identity, date sequenced, and/or sample characteristics obtained from sample metadata).

In some embodiments, each sample in a first subset of samples in the batch dataset has a corresponding first biopsy type, and each sample in a second subset of samples in the batch dataset has a corresponding second biopsy type. In some embodiments, first biopsy type or second biopsy type comprises a somatic biopsy selected from the set comprising macro dissected formalin fixed paraffin embedded (FFPE) tissue sections, surgical biopsy, skin biopsy, punch biopsy, prostate biopsy, bone biopsy, bone marrow biopsy, needle biopsy, CT-guided biopsy, ultrasound-guided biopsy, fine needle aspiration, aspiration biopsy, fresh tissue or blood samples.

In some embodiments, the first and second biopsy type is identified in respective metadata for each sample in the batch dataset. In order to provide a balanced cohort-matched reference dataset, each reference sample in a first subset of reference samples in the cohort-matched reference dataset has the corresponding first biopsy type, and each reference sample in a second subset of reference samples in the cohort-matched reference dataset has the corresponding second biopsy type. For example, if the plurality of samples in the batch dataset comprises 50% of samples with breast cancer, 20% of samples with lung cancer, and 30% of samples with brain cancer, then the cohort-matched reference dataset will incorporate the largest number of reference samples from the reference dataset that are compatible with these cancer type percentages. In some embodiments, similar methods of balancing a cohort-matched reference dataset with a batch dataset are employed with regards to other sample characteristics.

Referring to block 212 of FIG. 2A, in some embodiments, a linear or non-linear combination of the batch plurality of sequence features and the batch plurality of metadata features is determined by subjecting the batch plurality of sequence features and the batch plurality of metadata features to a dimension reduction technique. In some embodiments, the dimension reduction technique comprises Uniform Manifold Approximation and Projection (UMAP). In some embodiments, the dimension reduction technique comprises Principal Component Analysis (PCA).

Performing Global Quality Control Tests on Batch Dataset 122

Block 214.

Referring to block 214 of FIG. 2B, one or more global quality control tests (e.g., tests 152) are performed on the batch dataset using at least the cohort-matched reference dataset (e.g., batch). In some embodiments, the one or more global quality control tests comprise tests for one or more batch effects from a set comprising bioinformatics pipeline analysis and sequencing methods.

Referring to block 216 of FIG. 2B, in some embodiments, the one or more global batch quality control tests comprise tests for one or more batch effects from a set comprising bioinformatics pipeline analysis (e.g., date of sample analysis, sequencer identity, pipeline type, etc.), DNA contamination, sample handling (e.g., sample collection method, reagent changes, etc.) and sequencing methods (e.g., UMI vs UDI sequence adaptors).

In some embodiments, there are different bioinformatics pipelines used to analyze samples (e.g., based on biopsy type, cell-free nucleic acid samples), and the use of different pipelines can contribute to batch effects. For example, in some embodiments, even the type of test tube used for blood sample collection (e.g., PAX vs EDTA) is considered for possible impact on batch effects. In some embodiments, changes to instrumentation (e.g., sequencing machines or flow cells) can also contribute to batch effects. In some embodiments, reagents with potential batch effects include probe lots, controls (e.g., Horizon controls) and buffers.

Referring to block 218 of FIG. 2B, in some embodiments, the cohort-matched reference batch is used to adjust each sample in the batch dataset for one or more confounding covariates prior to performing the one or more global batch quality control tests. In some embodiments, this adjusting comprises normalization of expression levels for each gene in a reference genome (e.g., a reference genome shared each sample in the batch dataset and each reference sample in the cohort-matched reference batch) for each respective plurality to sequence reads for each sample in the batch dataset. In some embodiments, Mostafavi 2013 includes a summary of relevant normalization methods. See PLOS ONE, e68141 in section entitled "Unified Representation of Existing Normalization Methods."

In some embodiments, at least one sample in the batch dataset is a control sample (e.g., a Horizon control sample). In some embodiments, the at least one control sample in the batch dataset is used to adjust each other sample in the batch dataset. Horizon control samples are commercially available controls that are derived from cell lines comprising a known fusion variant. In some embodiments, the expression of the fusion variant is expected to be constant regardless of experimental conditions (e.g., sequencer identity, sequencing method, date of sequencing, etc.). These Horizon controls are useful for normalizing samples between and across batch datasets and also for providing information on sequencing trends over time (e.g., by comparing Horizon controls evaluated at different time points to each other). In some embodiments, any commercially available control sample can be used with methods described herein.

In some embodiments, a respective global batch quality control test comprises i) determining an average number of sequence reads per sample across the batch dataset, ii) obtaining a reference average number of sequence reads per sample from a reference dataset (e.g., or from the cohort-matched reference batch), and iii) comparing the average number of sequence reads across the batch dataset with the reference average number of sequence reads per sample. In some embodiments, when the average number of sequence reads falls below the reference average number of sequence reads per sample, the batch dataset fails the respective global batch quality control test.

In some embodiments, a respective global batch quality control test comprises i) determining an average percentage of mapped sequence reads per sample across the batch dataset, ii) obtaining a reference average percentage of mapped sequence reads per sample from a reference dataset (e.g., or from the cohort-matched reference batch), and iii) comparing the average percentage of mapped sequence reads across the batch dataset with the reference average percentage of mapped sequence reads per sample. In some embodiments, when the average percentage of mapped sequence reads falls below the reference average percentage of mapped sequence reads per sample, the batch dataset fails the respective global batch quality control test.

In some embodiments, the respective metadata for each sample in a batch dataset includes a respective cancer type. In some such embodiments, a respective global batch quality control test comprises applying, for each respective sample in the batch dataset, the corresponding plurality of sequence reads and corresponding metadata to a second trained classification model, the second trained classification model thereby providing a respective predicted cancer type for each sample. In some embodiments, the respective global batch quality control test further comprises comparing, for each sample, the respective cancer type from the respective metadata to the respective predicted cancer type. In some embodiments, one or more samples with a respective predicted cancer type that does not match the respective known cancer type, fail the global batch quality control test. In some embodiments, the entire batch dataset fails the respective global batch quality control test when one or more samples in the batch dataset fail the global batch quality control test. In some embodiments, the second trained classification method comprises any of the classification methods described in U.S. Provisional Patent Application No. 62/855,750 entitled 'Systems and Methods for Multi-Label Cancer Classification' and filed on May 31, 2019.

In some embodiments where the respective metadata for each sample in the batch dataset includes a respective cancer type, a respective global batch quality control test comprises determining a respective tumor purity percentage for each respective sample in the batch dataset. In some embodiments, tumor purity is determined based at least in part on variant allele fractions, and in some embodiments variant allele fractions are determined as described in Shin et al. 2017 "Prevalence and detection of low-allele-fraction variants in clinical cancer samples" Nat Comm 8, 1377. In some embodiments, when a respective sample has a corresponding tumor purity of less than 20%, less than 30%, less than 40%, or less than 50%, then the respective sample fails the respective global batch quality control test. In some embodiments, when at least 30%, at least 40%, at least 50%, or at least 60% of the plurality samples in the batch dataset have failed the respective global batch quality control test, then the batch dataset fails the global batch quality control test.

Block 220.

Referring to block 220 of FIG. 2B, respective samples from the batch dataset that fail any one of the one or more global quality control tests 152 are removed from the batch dataset or are flagged for manual inspection. In some embodiments, the removing step further comprises providing an updated batch dataset that lacks each of the respective samples that failed any one of the one or more global quality control tests.

Sample Reports

Referring to block 222, in some embodiments, for each sample in the batch of samples (in some embodiments, even those samples that fail a global batch quality control test), a respective sample report is provided. In alternative embodiments, sample reports are provided only for those samples that did not fail any one of the global batch quality control tests (e.g., samples included in the updated batch dataset). In some embodiments, each respective sample report comprises a least one of a set of expression calls, one or more matched therapies, or one or more matched clinical trials. In some embodiments, appropriate matched therapies are determined based on expression calls and cancer type information. In some embodiments, appropriate matched therapies are determined based on organoid tests. Examples of organoid tests and the correlation between organoid test results and therapy sensitivity are provided in U.S. Provisional Patent Application No. 62/924,621 entitled 'Systems and Methods for Predicting Therapeutic Sensitivity' and filed on Oct. 22, 2019. In some embodiments, appropriate matched clinical trials are determined based at least in part on corresponding expression calls for a respective sample.

In some embodiments, a sample report may further include summaries that provide patients and/or health care providers with a brief overview of the most important findings from the complete sample report. In some embodiments, a sample (e.g., patient) report is provided as described in U.S. Provisional Patent Application No. 62/855,750 entitled 'Systems and Methods for Multi-Label Cancer Classification' and filed on May 31, 2019.

In some embodiments, each sample in the batch of samples, after quality control analysis is performed, is further associated with corresponding clinical data. In some embodiments, the association between RNA sequence samples and clinical data is use to validate or refine expression calls. In some embodiments, clinical data comprises DNA mutations, patient response to therapy, organoid experiment results (e.g., organoids derived from a patient can be tested to determine if the organoids are sensitive to matched therapies), and/or histopathology images. Example histopathology images include H&E (hematoxylin and eosin) and IHC (immunohistochemistry) stained images.

Performing Single Sample Quality Control Tests

Block 230.

Referring to block 230 of FIG. 2B, in some embodiments, for each respective sample in the batch of samples, from the corresponding plurality of sequence reads, one or more single sample quality control tests are performed on the respective sample. Respective samples from the batch of samples that fail any one of the one or more single sample quality control tests are removed from the batch dataset or flagged for manual inspection. In some embodiments, any single sample quality control test can be applied to an entire batch dataset. In some embodiments, single sample QC tests are performed prior to batch QC tests. In some embodiments, single sample QC tests are performed after batch QC tests.

In some embodiments, a respective single sample quality control test compares the total number of sequence reads per sample in the batch of samples to the average number of sequence reads per reference sample in the entire reference dataset 140. In other words, in some embodiments, a respective single sample quality control test comprises i) determining an average number of sequence reads per sample across the batch dataset, and ii) obtaining a reference average number of sequence reads per sample from a reference dataset (e.g., or from the cohort-matched reference batch, or from a subset of the reference dataset). The respective single sample dataset compares the average number of sequence reads across the batch dataset with the reference average number of sequence reads per sample. In some embodiments, when the respective total number of sequence reads for a respective sample falls below the reference average number of sequence reads per sample, the respective sample fails the respective quality control test.

In some embodiments, a Wilcoxon test is used to evaluate whether the batch dataset fails the respective single sample quality control test. In some embodiments, a two-sample Wilcoxon test compares paired groups (e.g., compares most similar-paired-samples between two groups). For example, this is useful for directly comparing samples from a same set of subjects that are sequenced on both HiSeq1 and HiSeq2 systems. In some embodiments, an unpaired Wilcoxon test is used (e.g., in cases where there is some difference in the batches that are to be compared). In some embodiments, a modified p-value threshold is used to determine if there is a significant difference (e.g., a batch effect). In some embodiments, a modified p-value threshold is determined based on at least a plurality of high quality reference samples from the reference dataset 140. In some embodiments, a reference sample is determined to be high quality when the corresponding read number of the reference sample is at least 5 million sequence reads, at least 10 million sequence reads, at least 20 million sequence reads, at least 30 million sequence reads, at least 40 million sequence reads, at least 50 million sequence reads, at least 100 million sequence reads, or at least 200 million sequence reads.

In some embodiments, a respective single sample quality control test comprises applying, for each respective sample in the batch dataset, the corresponding plurality of sequence reads and corresponding sample metadata to a first trained classification model, the first trained classification model thereby providing a set of predicted gender assignments comprising a respective predicted gender assignment for each sample. In some embodiments, the respective single sample quality control test further comprises comparing the set of predicted gender assignments to an expected set of gender assignments (e.g., to detect unintentional sample swaps). In some embodiments, one or more samples with a respective predicted gender assignment that does not match the expected set of gender assignments (e.g., too high of a proportion of one gender) fails the respective single sample quality control test. In some embodiments, the entire batch dataset fails the respective single sample quality control test when the set of predicted gender assignments does not match the expected set of gender assignments (e.g., when there appear to be too many sample swaps).

In some embodiments, by way of non-limiting example, the first classification model comprises a decision tree. Decision tree algorithms suitable for use as the classifier of block 244 are described in, for example, Duda, 2001, *Pattern Classification*, John Wiley & Sons, Inc., New York, pp. 395-396, which is hereby incorporated by reference. In some embodiments, the decision tree is random forest regression. One specific algorithm that can be used as the classifier of block 244 is a classification and regression tree (CART). Other examples of specific decision tree algorithms that can be used as the classifier of block 244 include, but are not limited to, ID3, C4.5, MART, and Random Forests.

CART, ID3, and C4.5 are described in Duda, 2001, *Pattern Classification*, John Wiley & Sons, Inc., New York. pp. 396-408 and pp. 411-412, which is hereby incorporated by reference. CART, MART, and C4.5 are described in Hastie et al., 2001, *The Elements of Statistical Learning*, Springer-Verlag, New York, Chapter 9, which is hereby incorporated by reference in its entirety. Random Forests are described in Breiman, 1999, "Random Forests—Random Features," Technical Report 567, Statistics Department, U.C. Berkeley, September 1999, which is hereby incorporated by reference in its entirety.

In some embodiments, a respective single sample quality control test in the one or more single sample quality control tests comprises i) determining, for each respective sample in the batch of samples, a respective number of non-duplicated mapped sequence reads (e.g., reads that are not the result of PCR duplication) in the plurality of sequence reads, and ii) comparing the respective number of non-duplicated mapped sequence reads with an expected number of non-duplicated mapped sequence reads. Each non-duplicated mapped sequence read maps to a corresponding portion of a reference genome (e.g., has unique start and end sites in a reference genome). In some embodiments, when the respective number of non-duplicated mapped sequence reads falls below a predetermined number of non-duplicated mapped reads, the respective sample fails the respective single sample quality control test.

In some embodiments, the expected number of non-duplicated mapped sequence reads is predicated on whether the sample was obtained from a solid or liquid biopsy of the subject (e.g., from a solid tumor or from a blood sample). In some embodiments, a respective number of duplicate reads is determined for each sample in the batch dataset (e.g., by identifying sequence reads that have identical start and end sites). In some embodiments, the method further provides a graphical representation of the respective number of duplicate reads as part of a sample report or global batch report.

In some embodiments, a respective single sample quality control test comprises determining a respective quality score for each base pair read position in the corresponding plurality of sequence reads of each respective sample in the batch dataset. In some embodiments, when one or more respective quality scores of one or more respective base pair read positions fall below a threshold quality score, the respective sample fails the respective single sample quality control test. In some embodiments, the threshold quality score comprise 20.0 (e.g., as computed by FastQC). In some embodiments, a respective quality score is determined for each sequence read in the plurality of sequence reads for each respective sample in the batch dataset, and in some such embodiments, one or more sequence reads with corresponding quality scores that fall below a threshold read quality score are discarded.

In some embodiments, a respective single sample quality control test comprises determining an average quality score for each sequence read in the corresponding plurality of sequence reads of each respective sample in the batch dataset. In some embodiments, when a mean over the average quality scores across the corresponding plurality of sequence reads falls below a threshold quality score, the respective sample fails the respective single sample quality control test. In some embodiments, the threshold quality score comprise 20.0 (e.g., as computed by FastQC).

In some embodiments, a respective single sample quality control test comprises, for each respective sample in the batch of samples, determining a respective percentage of properly paired sequence reads (e.g., the percentage of sequence reads that are paired-end reads and are properly paired), where, when the percentage of properly paired sequence reads falls below a predetermined paired read threshold, the respective sample fails the respective single sample quality control test. In some embodiments, the predetermined paired read threshold comprises at least 90%, at least 95%, or at least 99%.

In some embodiments, a respective single sample quality control test comprises determining, for each respective sample in the batch of samples, a respective number of expressed genes (e.g., the number of genes that have non-zero supporting sequence reads). In some embodiments, when the corresponding expressed reads score falls below a predetermined number of expressed reads, the respective sample fails the respective single sample quality control test. In some embodiments, when the respective sample is derived from a solid biopsy, the predetermined number of expressed genes is at least 18,000, at least 19,000, or at least 20,000 genes. In some embodiments, when the respective sample is derived from a liquid (e.g., hematological) biopsy the predetermined number of expressed genes is at least 15,000, at least 16,500, or at least 17,000 genes. Some cancer types comprise different sets of expressed genes (e.g., some cancer types are transcriptionally distinct). See e.g., Li et al. 2017 "Transcriptional landscape of human cancers" Oncotarget 8(21), 34534-34551. In some embodiments, the predetermined number of expressed genes is determined at least in part based on cancer type (e.g., from corresponding metadata) of the respective sample.

In some embodiments, a respective single sample quality control test comprises determining, for a respective sample in the batch of samples, a respective GC content of the corresponding plurality of sequence reads. In some embodiments, when the respective GC content is outside of a predetermined GC content threshold, the respective sample fails the respective single sample quality control test. In some embodiments, the predetermined GC content threshold comprises 35-60%, 40-60%, 45-60%, 50-60%, or 55-60%. GC content varies widely across genes in the human genome. See e.g., Versteeg et al. 2003 "The Human Transcriptome Map Reveals Extremes in Gene Density, Intron Length, GC content, and Repeat Patterns for Domains of Highly and Weekly Expressed Genes" Genome Res 13(9), 1998-2004. GC content can affect how well a nucleic acid molecule is amplified during PCR. See e.g., Mammedov et al. 2009 "A Fundamental Study of the PCR Amplification of GC-Rich DNA Templates" Comput Biol Chem 32(6), 452-457.

In some embodiments, a respective single sample quality control test comprises determining, for each respective sample in the batch of samples, a respective per base sequence content analysis across the corresponding plurality of sequence reads of the respective sample. In some embodiments, a respective sample fails the respective single sample quality control test when a distribution of A, T, C or G content drifts by more than a threshold percentage across the base positions collectively represented by the corresponding plurality of sequence reads for the respective sample. In some embodiments, the threshold percentage comprises at least 5%, at least 6%, at least 7%, at least 8%, at least 9%, or at least 10% drift as determined from FastQC.

In some embodiments, a respective single sample quality control test comprises determining, for each respective sample in the batch of samples, a respective per base GC content analysis across the corresponding plurality of sequence reads. In some embodiments, a respective sample fails the respective single sample quality control test when a distribution of the GC content drifts by more than a threshold percentage across the base positions collectively represented by the corresponding plurality of sequence reads. In some embodiments, the threshold percentage comprises more than 5%, more than 6%, more than 7%, more than 8%, more than 9%, or more than 10% drift.

In some embodiments, a respective single sample quality control test comprises determining, for each respective sample in the batch of samples, a corresponding distribution of per sequence read GC content across the corresponding plurality of sequence reads. In some embodiments, a respective sample fails the respective single sample quality control test when a goodness of fit test determines that the respective distribution of per sequence read GC content deviates from a normal distribution at a threshold significance level (e.g., by analysis with a Chi-square Goodness of Fit test at the 0.05 significance level).

In some embodiments, a respective single sample quality control test comprises determining, for each respective sample in the batch of samples, a corresponding per base missing content analysis across the corresponding plurality of sequence reads that determines a percentage of missing calls for each base position represented by the corresponding plurality of sequence reads. In some embodiments, a respective sample fails the respective single sample quality control test when the corresponding percentage of missing calls for a base position represented by the corresponding plurality of sequence reads exceeds a threshold percentage. In some embodiments, the threshold percentage comprises more than 10%, more than 15%, more than 20%, or more than 25%.

In some embodiments, a respective single sample quality control test comprises a sequence read length distribution analysis that determines, for each respective sample in the batch dataset, a respective range of sequence read lengths across the corresponding plurality of sequence reads. In some embodiments, a respective sample fails the respective single sample quality control test when the respective range of sequence read lengths deviates from a sequence read expectation (e.g., if fixed length sequence reads, flag/remove if a distribution of sequence read lengths is observed, if ranges of sequence reads observed, flag/remove if the distribution does not satisfy an expectation value for the distribution).

In some embodiments, a respective single sample quality control test comprises an overrepresented sequence analysis that determines, for each respective sample in the batch dataset, whether any sequence reads in the corresponding plurality of sequence reads are overrepresented. In some embodiments, a respective sample fails the respective single sample quality control test when the overrepresented sequence analysis identifies one or sequence read sequences that are represented by more than a threshold percentage of the corresponding plurality of sequence reads. In some such embodiments, the threshold percentage comprises at least 0.05%, at least 0.10%, at least 0.15%, or at least 0.2%.

Segmenting Modules into Containers

Block 240.

Referring to block 240 of FIG. 2B, in some embodiments, the one or more batch quality control tests (e.g., entire batch outlier detection) comprise a first module (e.g., module 120), and the one or more single sample quality control tests (e.g., single sample outlier detection) comprise a second module (e.g., module 121). In some embodiments, each of the first module and the second module comprise a respective docker (e.g., a computational container that enables the performance of the batch quality control tests and the single sample quality control tests regardless of operating system 116). In some embodiments, the first module and the second module are performed at a same computer system. In some embodiments, the first module and the second module are performed at different computer systems.

Examples of dockers (also described as 'containers' or 'docker containers') are provided by Boettiger 2015 "An introduction to Docker for reproducible research, with examples from the R environment" arXiv: 1410.0846v1 and Felter et al. 2014 "An updated performance comparison of virtual machines and linux containers" in IEEE International Sympo. Docker containers are often useful to facilitate workflow, and can enable the coordinated use of multiple applications. See e.g., Di Tommaso et al 2015 "The impact of Docker containers on the performance of genomic pipelines" PeerJ 3: e1273. In some embodiments, the use of two or more dockers (e.g., modules or containers) provides flexibility to the performance of methods described herein (e.g., ease of application without regard to type of operating system available).

In some embodiments, the first module 120 (e.g., the batch quality control module) tests the global transcriptome quality of a batch of RNA samples (e.g., a plurality of samples from a whole flowcell or a set of flowcells). In some embodiments, the first module 120 evaluates global transcriptome quality of a batch of RNA samples against a balanced set of samples from a reference (e.g., a cohort matched reference batch).

In some embodiments, inputs to the first module 120 comprise, for each sample in the batch of samples, i) a corresponding plurality of sequence reads and ii) corresponding metadata (e.g., including at least one or more bioinformatics values). In some embodiments, each plurality of sequence reads is normalized (e.g., as described above with regards to block 218). In some embodiments, the first module 120 includes or has access to reference data (e.g., reference dataset 140). In some embodiments, the reference dataset 140 comprises a plurality of reference samples 142 including, for each reference sample in the plurality of reference samples, a corresponding plurality of sequence reads 144 and corresponding reference metadata 146.

In some embodiments, a corresponding plurality of sequence reads 144 comprises a .csv file or a .parquet file. In some embodiments, a corresponding plurality of sequence reads 144 comprises any file format known in the art. In some embodiments, bioinformatics values included in sample metadata comprise LIMS (e.g., Laboratory Information Management Systems) values.

In some embodiments, global batch quality control tests evaluated by the first module comprise statistical tests and/or dimensionality reduction. In some embodiments, these statistical tests comprise any method to distinguish between a batch dataset 122 and a corresponding cohort-matched reference batch 130. In some embodiments, the statistical batch quality control tests are performed on a subset of the batch dataset and corresponding cohort-matched reference batch (e.g., only samples of a particular cancer type are compared).

In some embodiments, the evaluation of one or more batch quality tests over time comprises a third module, and in some embodiments, this third module comprises a respective third docker. In some embodiments, the third module evaluates trends in batches of RNA sequences over time (e.g., at multiple points in time). This is useful both to ensure stability of sequencing methods (e.g., by evaluating whether control samples are similar across time points).

In some embodiments, the method further provides (e.g., subsequent to the application of module 120) a global batch quality control report. In some embodiments, the global batch report comprises at least i) a list of one or more samples from the batch dataset that fail any one of the one or more bath quality control tests, and ii) a list of one or more reference samples from the reference dataset 140 that were evaluated within a predefined time period (e.g., as identified from corresponding reference sample metadata).

In some embodiments, this predefined time period comprises at least 1 day, at least 2 days, at least 3 days, at least 4 days, at least 5 days, at least 6 days, at least 7 days, at least 10 day at least 14 days, at least 21 days, at least 28 days, or at least 30 days. In some embodiments, the global batch report is provided by the third module. In some embodiments, a respective global batch report is provided at least every 1 day, at least every 1 week, at least every 2 weeks, at least every 1 month, at least every 3 months, or at least every 1 year.

In some embodiments, quality metrics evaluated by the third module comprise one or more metrics from the set of at least GC content, contamination levels (e.g., in particular DNA contamination that results from inadequate DNase application of the biological sample), read number, percentage of mapped reads, gene duplication rate, number of genes expressed as a function of read number, transcript integrity number, accuracy of tumor of unknown origin determination, or accuracy of gender prediction.

In some embodiments, the third module further provides graphical representations of one or more metric evaluation results as compared with one or more of the set comprising time, pipeline version, sequencer type, flow cell, or cancer type. In some embodiments, these graphical representations comprise any graphical representation described elsewhere herein or known in the art.

In some embodiments, the method further provides one or more graphical representations for overall features of the batch dataset. In some embodiments, a respective graphical representation includes detailed information regarding the corresponding batch dataset feature. In some embodiments, the method provides one or more graphical representations of the results of one or more global batch quality control test performed in accordance with embodiments described herein. In some embodiments, the method provides one or more graphical representations of the results of one or more single sample quality control test performed in accordance with embodiments described herein. In some embodiments, a batch dataset feature comprises a combination of the respective metadata features for each respective sample in the batch of samples of the batch dataset. For example, in some embodiments, the metadata features of each sample in a batch dataset are combined to provide an overall metric (e.g., feature) for the batch dataset.

Identification of Technical Batch Effects in an RNA Expression Pipeline

Another aspect of the present disclosure provides a method of performing quality control, at a computer system having one or more processors, and memory storing one or more programs for execution by the one or more processors. The method includes obtaining, in electronic form, a batch dataset comprising, for each respective test sample in a batch of test samples, a corresponding expression profile including a corresponding gene expression value for each respective gene in a first set of genes, and a corresponding set of metadata comprising values for each respective characteristic in a first set of characteristics about a sample.

The method includes determining for the batch dataset, a cohort-matched reference dataset including, for each respective reference sample in a plurality of reference samples, a corresponding expression profile comprising a corresponding gene expression value for each respective gene in the first set of genes. Each respective reference sample in the plurality of reference samples is associated with a corresponding set of metadata comprising a corresponding value for each respective characteristic in a second set of characteristics about the respective reference sample. The aggregate values for each respective characteristic in a third set of one or more characteristics that are present in both the first set of characteristics and the second set of characteristics is balanced between the batch dataset and the cohort-matched reference dataset.

Dimension reduction is performed on a combined dataset consisting of the corresponding expression profile for each respective test sample in the plurality of test samples and the corresponding expression profile for each respective reference sample in the plurality of reference samples. Thus, there is obtained for each respective test sample and each respective reference sample, a corresponding set of coordinates embedded in a lower dimensional-space than the dimensions of the corresponding expression profile.

The method further includes determining a statistical measure of similarity between the sets of coordinates obtained for the test samples and the sets of coordinates obtained for the reference samples. The statistical measure of similarity is compared to a threshold value, and the batch dataset is validated for reporting when the statistical measure of similarity satisfies the threshold value, or not validated when the statistical measure of similarity does not satisfy the threshold value.

Figure 15:
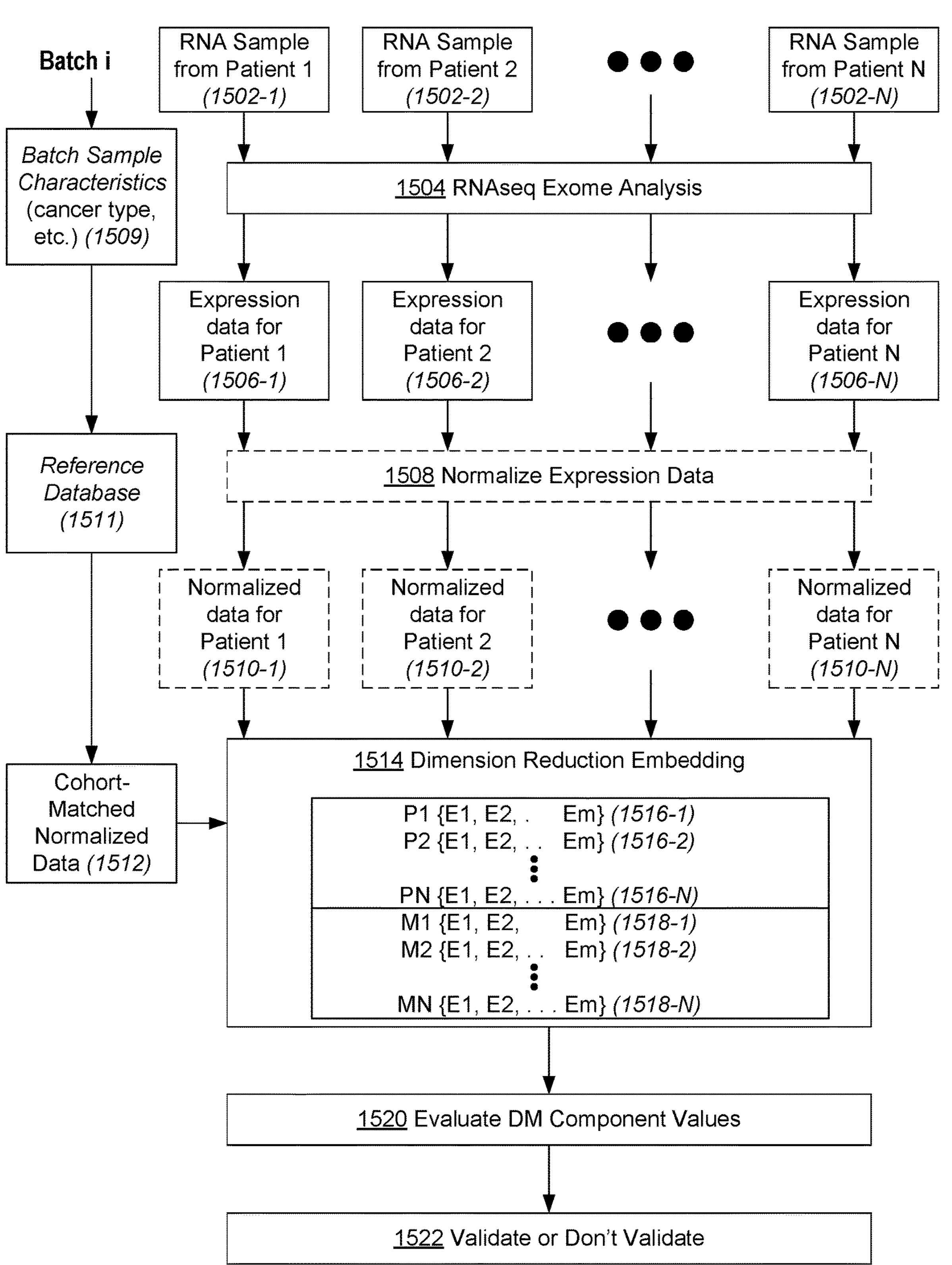
FIG. 15 illustrates an example method for performing quality control on a batch of samples, in accordance with some embodiments of the present disclosure.

For example, FIG. 15 illustrates a method of performing quality control (e.g., on a batch of samples compared to a reference dataset), in accordance with some embodiments of the present disclosure. A batch dataset is obtained from a batch of test samples (e.g., "Batch i"), including a plurality of RNA samples from a plurality of N patients 1502 (e.g., 1502-1, 1502-2, . . . , 1502-N). In some embodiments, referring to Block 1504, the batch dataset is obtained using a sequencing analysis of the test samples (e.g., RNAseq Exome Analysis). The batch dataset includes an expression profile for each test sample, where each expression profile includes expression data for each respective patient 1506 in the plurality of N patients (e.g., 1506-1, 1506-2, . . . 1506-N). In some embodiments, the expression data includes a corresponding gene expression value for each respective gene in a plurality of genes in the test sample (e.g., as sequenced by RNAseq). In some embodiments, the expression data further includes metadata indicating values for a plurality of characteristics associated with the test sample, such as RNA transcription profiles (e.g., as determined from a plurality of sequence reads), clinical data (e.g., patient diagnosis, treatment outcomes, etc.), gender, biopsy type (e.g., heme vs. solid biopsy), molecular data (e.g., genomic mutations), and/or other characteristics (e.g., tissue site, tumor purity, cancer type, collection method, sequencer identity, and/or date sequenced).

In some embodiments, referring to Block 1508, the expression data in each respective expression profile is normalized. In some embodiments, normalization of the expression data in each expression profile generates a plurality of normalized datasets 1510 (e.g., 1510-1, 1510-2, . . . , 1510-N).

In some embodiments, the method further includes obtaining a cohort-matched reference dataset 1512 for a plurality of reference samples. In some embodiments, the cohort-matched reference dataset is identified by matching the proportion of one or more characteristics 1509 of the samples in the batch dataset with reference samples, e.g., in a reference database 1511, having the same proportion of those one or more characteristics (e.g., tissue site, tumor purity, cancer type, collection method, sequencer identity, date sequenced, clinical data (e.g., patient diagnosis, treatment outcomes, etc.), gender, biopsy type (e.g., heme vs. solid biopsy), molecular data (e.g., genomic mutations), and/or other characteristics). The cohort-matched reference dataset includes an expression profile for each reference sample in the plurality of reference samples. Each respective expression profile includes a corresponding gene expression value for each respective gene in the plurality of genes (e.g., where the plurality of genes included in each reference sample expression profile is the same as the plurality of genes included in each test sample expression profile).

In some embodiments, the plurality of reference samples comprises the same number of reference samples as the number of test samples in the batch of test samples (e.g., N reference samples). In some embodiments, the plurality of reference samples is selected for the batch of test samples based on one or more similarities between characteristics associated with the reference samples and the test samples (e.g., tissue site, tumor purity, cancer type, collection method, sequencer identity, and/or date sequenced). In some embodiments, the metadata (e.g., values for characteristics) between the batch of test samples and the plurality of reference samples are balanced such that the distribution (e.g., proportions) of test sample characteristics amongst the plurality of test samples in the batch of test samples are similar to the distribution (e.g., proportions) of reference sample characteristics amongst the plurality of reference samples.

In some embodiments, the cohort-matched reference dataset is normalized.

In accordance with the method, referring to Block 1514, dimension reduction (e.g., PCA, latent component analysis, partial least squares regression, etc.) is performed on a combined dataset consisting of the corresponding expression profile for each respective test sample in the plurality of test samples and the corresponding expression profile for each respective reference sample in the plurality of reference samples. For each respective test sample P and each respective reference sample M, a corresponding set of coordinates 1516-1518 is embedded in a lower dimensional-space (e.g., m-space) than the dimensions of the corresponding expression profile (e.g., 1516-1, 1516-2, . . . , 1516-N, and 1518-1, 1518-2, . . . , 1518-N).

Referring to Block 1520, the method further includes evaluating the component values using the combined dataset following dimensionality reduction. The method includes determining a statistical measure of similarity between the sets of coordinates obtained for the test samples and the sets of coordinates obtained for the reference samples, and comparing the statistical measure of similarity to a threshold value. Referring to Block 1522, the batch dataset is validated for reporting when the statistical measure of similarity satisfies the threshold value, and in not validated when the statistical measure of similarity does not satisfy the threshold value. In some embodiments, when the statistical measure of similarity does not satisfy the threshold value, the batch dataset is flagged for rejection and/or further evaluation of batch effects. In some embodiments, further analysis identifies individual samples or groups of individual samples in the batch dataset that are driving the dissimilarity with the reference samples. In some embodiments, one or more of these samples driving the statistical difference is removed from the batch dataset, the global quality control test is rerun with the modified batch dataset (e.g., in which the individual samples contributing to the statistical dissimilarity have been removed), and the modified dataset is validated if it passes the batch quality control test. In some embodiments, when one or more sample is identified as contributing to an identified batch effect, correction factors are determined and applied in order to normalize the one or more samples to the reference dataset. In this fashion, these samples can be validated and used for downstream analysis. In some embodiments, when one or more sample is identified as contributing to an identified batch effect, the one or more samples are rejected (e.g., after manual inspection or automatically). In some embodiments, rejected samples are rerun through the RNA expression pipeline.

It should be noted that details of other processes described herein with respect to other methods described herein (e.g., those methods shown in FIGS. 2, 16, and 17) are also applicable in an analogous manner to the method described above with respect to FIG. 15. For example, details relating to data collection, data processing, cohort-matching, dimension-reduction analysis, etc., described above with reference to the method outlined in FIG. 15 optionally have one or more of the characteristics of the data collection, data processing, cohort-matching, dimension-reduction analysis, etc., described herein with reference to other methods described herein (e.g., those outlined in FIGS. 2, 16, and 17). For brevity, these details are not repeated here.

Validation of a Change to a Bioinformatics Pipeline

Another aspect of the present disclosure provides a method of validating a change in an RNA expression pipeline, at a computer system having one or more processors, and memory storing one or more programs for execution by the one or more processors. The method includes obtaining, in electronic form, a batch dataset comprising, for each respective test sample in a batch of test samples, a corresponding expression profile prepared using a first RNA expression pipeline. The corresponding expression profile includes a corresponding gene expression value for each respective gene in a first set of genes. The batch dataset further comprises a corresponding set of metadata comprising values for each respective characteristic in a first set of characteristics about the respective test sample.

The method includes determining for the batch dataset, a cohort-matched reference dataset including, for each respective reference sample in a plurality of reference samples, a corresponding expression profile prepared using a second RNA expression pipeline (e.g., the pipeline existing prior to the change), comprising a corresponding gene expression value for each respective gene in the first set of genes. Each respective reference sample in the plurality of reference samples is associated with a corresponding set of metadata comprising a corresponding value for each respective characteristic in a second set of characteristics about the respective reference sample. The aggregate values for each respective characteristic in a third set of one or more characteristics that are present in both the first set of characteristics and the second set of characteristics is balanced between the batch dataset and the cohort-matched reference dataset.

Dimension reduction is performed on a combined dataset consisting of the corresponding expression profile for each respective test sample in the plurality of test samples and the corresponding expression profile for each respective reference sample in the plurality of reference samples. Thus, there is obtained for each respective test sample and each respective reference sample, a corresponding set of coordinates embedded in a lower dimensional-space than the dimensions of the corresponding expression profile.

The method further includes determining a statistical measure of similarity between the sets of coordinates obtained for the test samples and the sets of coordinates obtained for the reference samples. The statistical measure of similarity is compared to a threshold value, and the change in the RNA expression pipeline is validated when the statistical measure of similarity satisfies the threshold value, or the change in the RNA expression pipeline is not validated when the statistical measure of similarity does not satisfy the threshold value.

Figure 16:
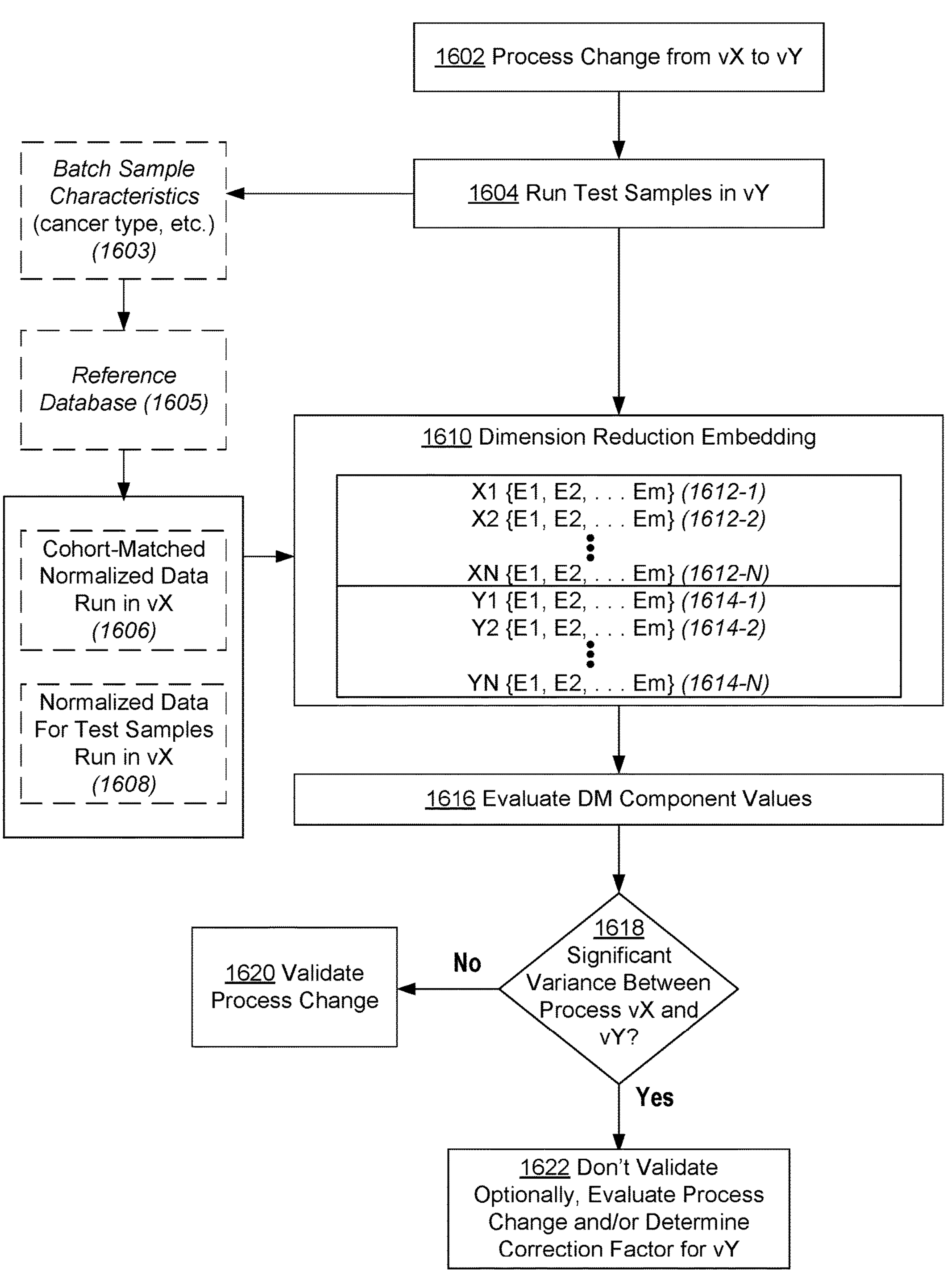
FIG. 16 illustrates an example method for validating a change in a bioinformatics pipeline, e.g., an RNA expression pipeline, in accordance with some embodiments of the present disclosure.

For example, FIG. 16 illustrates a method of validating a change in an RNA expression pipeline, in accordance with some embodiments of the present disclosure (e.g., determining usability of a new process and/or determining a correction factor for a new process). A batch dataset is obtained from a batch of test samples, where the batch dataset includes a corresponding expression profile for each respective test sample in the batch of test samples. In some embodiments, each respective expression profile includes a corresponding gene expression value for each respective gene in a plurality of genes in the test sample (e.g., as determined by an RNA expression pipeline). In some embodiments, each respective expression profile further includes metadata indicating values for a plurality of characteristics associated with the test sample, such as RNA transcription profiles (e.g., as determined from a plurality of sequence reads), clinical data (e.g., patient diagnosis, treatment outcomes, etc.), gender, biopsy type (e.g., heme vs. solid biopsy), molecular data (e.g., genomic mutations), and/or other characteristics (e.g., tissue site, tumor purity, cancer type, collection method, sequencer identity, and/or date sequenced).

In some embodiments, each expression profile is prepared using a sequencing analysis (e.g., an RNA expression pipeline) of each respective test sample in the batch of test samples. In some embodiments, each respective test sample in the batch of test samples is subjected to a first sequencing analysis (e.g., a first RNA expression pipeline, "vX"). Referring to Block 1602, in some embodiments, a process change in the RNA expression pipeline comprises changing the sequencing analysis from a first process (e.g., vX) to a second process (e.g., vY). Referring to Block 1604, in some embodiments, each respective test sample in the batch of test samples is further subjected to a second sequencing analysis (e.g., a second RNA expression pipeline, "vY").

Thus, in some embodiments, the method comprises obtaining a first batch dataset 1608 (e.g., a vX batch dataset) including, for each respective test sample in the batch of test samples, a corresponding first expression profile obtained using a first process (e.g., vX) and a second batch dataset (e.g., a vY batch dataset) including, for each respective test sample in the batch of test samples, a corresponding second expression profile obtained using a second process (e.g., vY).

In some embodiments, the expression data in each respective first expression profile in the first batch dataset and the expression data in each respective second expression profile in the second batch dataset are normalized.

In some embodiments, the method further includes obtaining a cohort-matched reference dataset 1606 for a plurality of reference samples. In some embodiments, the cohort-matched reference dataset is identified by matching the proportion of one or more characteristics 1603 of the samples in the batch dataset with reference samples, e.g., in a reference database 1605, having the same proportion of those one or more characteristics (e.g., tissue site, tumor purity, cancer type, collection method, sequencer identity, date sequenced, clinical data (e.g., patient diagnosis, treatment outcomes, etc.), gender, biopsy type (e.g., heme vs. solid biopsy), molecular data (e.g., genomic mutations), and/or other characteristics). The cohort-matched reference dataset includes an expression profile for each reference sample in the plurality of reference samples. Each respective expression profile includes a corresponding gene expression value for each respective gene in the plurality of genes (e.g., where the plurality of genes included in each reference sample expression profile is the same as the plurality of genes included in each test sample expression profile).

In some embodiments, the cohort-matched reference dataset is a sample-matched dataset 1608. That is, in some embodiments, the same samples are run through both versions of the RNA expression pipeline, and compared to each other as the batch dataset (e.g., generated from the samples run through the new version of the RNA expression pipeline) and reference dataset (e.g., generated from the samples run through the previous version of the RNA expression pipeline).

In some embodiments, the plurality of reference samples is selected for the batch of test samples based on one or more similarities between characteristics associated with the reference samples and the test samples processed using process vY (e.g., tissue site, tumor purity, cancer type, collection method, sequencer identity, and/or date sequenced). In some embodiments, the metadata (e.g., values for characteristics) between the batch of test samples and the plurality of reference samples are balanced such that the distribution (e.g., proportions) of test sample characteristics amongst the plurality of test samples processed using process vY are similar to the distribution (e.g., proportions) of reference sample characteristics amongst the plurality of reference samples.

In some embodiments, the cohort-matched reference dataset is normalized.

In accordance with the method, referring to Block 1610, dimension reduction (e.g., PCA, latent component analysis, partial least squares regression, etc.) is performed on a combined dataset including the corresponding second expression profile for each respective test sample, processed using process vY, in the plurality of test samples and the corresponding expression profile for each respective reference sample, processed using process vX, in the cohort-matched reference dataset. In some embodiments, the combined dataset further includes the corresponding first expression profile for each respective test sample processed using process vX in the plurality of test samples.

Thus, for each respective test sample and each respective reference sample processed using process vX, and for each respective test sample processed using process vY, a corresponding set of coordinates 1612-1614 is embedded in a lower dimensional-space (e.g., m-space) than the dimensions of the corresponding expression profile (e.g., 1612-1, 1612-2, . . . , 1612-N, and 1614-1, 1614-2, . . . , 1614-N).

Referring to Block 1616, the method further includes evaluating the component values using the combined dataset following dimensionality reduction. The method includes determining a statistical measure of similarity between the sets of coordinates obtained for the test samples and the reference samples processed using process vX, and the test samples processed using process vY. Referring to Block 1618, the statistical measure of similarity is compared to a threshold value to determine if there is significant variance between process vX and process vY. Referring to Block 1620, the change in the RNA expression pipeline is validated when the statistical measure of similarity satisfies the threshold value. Referring to Block 1622, the change in the RNA expression pipeline is rejected and/or flagged for further evaluation of the process change and/or for determination of a correction factor for process vY when the statistical measure of similarity does not satisfy the threshold value.

It should be noted that details of other processes described herein with respect to other methods described herein (e.g., those methods shown in FIGS. 2, 15, and 17) are also applicable in an analogous manner to the method described above with respect to FIG. 16. For example, details relating to data collection, data processing, cohort-matching, dimension-reduction analysis, etc., described above with reference to the method outlined in FIG. 16 optionally have one or more of the characteristics of the data collection, data processing, cohort-matching, dimension-reduction analysis, etc., described herein with reference to other methods described herein (e.g., those outlined in FIGS. 2, 15, and 17). For brevity, these details are not repeated here.

Expansion of Reference Database

Another aspect of the present disclosure provides a method of adding RNA expression data to a reference database, at a computer system having one or more processors, and memory storing one or more programs for execution by the one or more processors. The method includes obtaining, in electronic form, a new expression dataset. The new expression dataset includes, for each respective test sample in a plurality of test samples, a corresponding expression profile prepared using a first RNA expression pipeline, where the corresponding expression profile comprises a corresponding gene expression value for each respective gene in a first set of genes. The new expression dataset further includes a corresponding set of metadata including values for each respective characteristic in a first set of characteristics about the respective test sample.

The method includes determining for the new expression dataset, a cohort-matched reference dataset including, for each respective reference sample in a plurality of reference samples, a corresponding expression profile comprising a corresponding gene expression value for each respective gene in the first set of genes. Each respective reference sample in the plurality of reference samples is associated with a corresponding set of metadata comprising a corresponding value for each respective characteristic in a second set of characteristics about the respective reference sample. Each expression profile corresponding to a reference sample in the plurality of reference samples is from the reference database. The aggregate values for each respective characteristic in a third set of one or more characteristics that are present in both the first set of characteristics and the second set of characteristics is balanced between the batch dataset and the cohort-matched reference dataset.

Dimension reduction is performed on a combined dataset consisting of the corresponding expression profile for each respective test sample in the plurality of test samples and the corresponding expression profile for each respective reference sample in the plurality of reference samples. Thus, there is obtained for each respective test sample and each respective reference sample, a corresponding set of coordinates embedded in a lower dimensional-space than the dimensions of the corresponding expression profile.

The method further includes determining a statistical measure of similarity between the sets of coordinates obtained for the test samples and the sets of coordinates obtained for the reference samples, and the statistical measure of similarity is compared to a threshold value. The method includes adding the new expression data set to the reference database when the statistical measure of similarity satisfies the threshold value, or, when the statistical measure of similarity does not satisfy the threshold value, determining a set of conversion factors for normalizing the expression profiles in the new expression data set against expression profiles in the reference database, normalizing the expression profiles in the new expression data set using the set of conversion factors, thus obtaining a normalized new expression data set, and adding the normalized new expression data set to the reference database.

Figure 17:
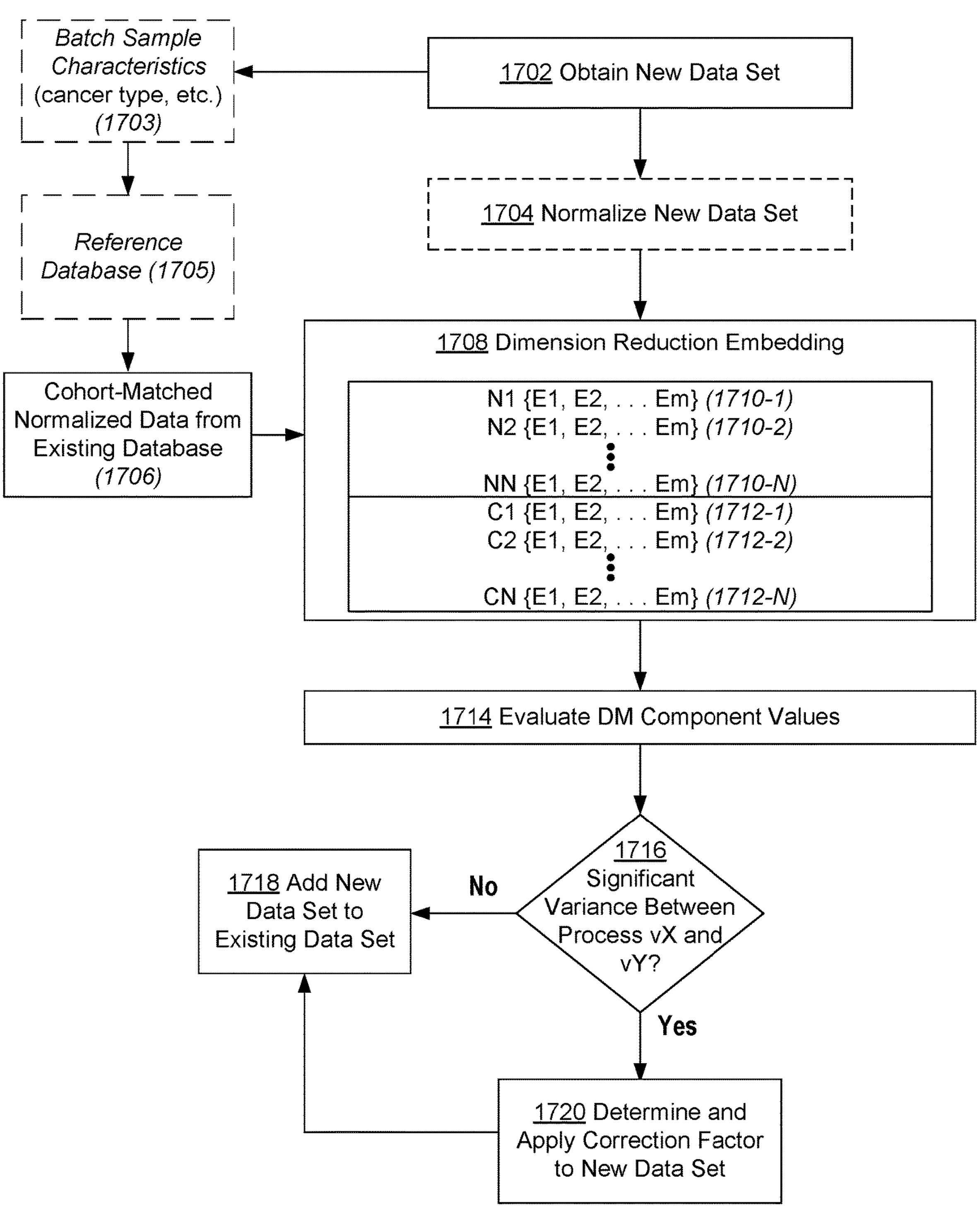
FIG. 17 illustrates an example method for expanding a reference database, in accordance with some embodiments of the present disclosure.

For example, FIG. 17 illustrates a method of adding RNA expression data to a reference database, in accordance with some embodiments of the present disclosure (e.g., validating newly acquired expression data to be used in updating a reference database).

Referring to Block 1702, a new expression dataset (e.g., of RNA expression data) is obtained. In some embodiments, the new expression dataset includes, for each respective test sample in a plurality of test samples, an expression profile prepared using a first RNA expression pipeline and including gene expression values for a plurality of genes. The new expression dataset further includes a corresponding set of metadata including values for characteristics associated with the test sample.

Referring to Block 1704, in some embodiments, the new expression dataset is normalized.

In some embodiments, the method further includes obtaining a cohort-matched reference dataset 1706 for the new expression dataset. In some embodiments, the cohort-matched reference dataset is identified by matching the proportion of one or more characteristics 1703 of the samples in the batch dataset with reference samples, e.g., in a reference database 1705, having the same proportion of those one or more characteristics (e.g., tissue site, tumor purity, cancer type, collection method, sequencer identity, date sequenced, clinical data (e.g., patient diagnosis, treatment outcomes, etc.), gender, biopsy type (e.g., heme vs. solid biopsy), molecular data (e.g., genomic mutations), and/or other characteristics). The cohort-matched reference dataset includes an expression profile for each reference sample in the plurality of reference samples. Each respective expression profile includes a corresponding gene expression value for each respective gene in the plurality of genes (e.g., where the plurality of genes included in each reference sample expression profile is the same as the plurality of genes included in each test sample expression profile).

In some embodiments, the cohort-matched reference dataset includes an expression profile for each reference sample in a plurality of reference samples. In some embodiments, each respective expression profile is from the reference database (e.g., an existing database) and includes a corresponding gene expression value for each respective gene in the plurality of genes (e.g., as included in the new expression dataset).

Each respective reference sample in the plurality of reference samples is associated with a corresponding set of metadata including values for characteristics associated with the reference sample. In some embodiments, the cohort-matched reference dataset is matched (e.g., balanced) according to any of the methods described in FIGS. 15 and/or 16.

In some embodiments, the cohort-matched reference dataset is normalized.

In accordance with the method, referring to Block 1708, dimension reduction (e.g., PCA, latent component analysis, partial least squares regression, etc.) is performed on a combined dataset consisting of the corresponding expression profile for each respective test sample in the plurality of test samples and the corresponding expression profile for each respective reference sample in the plurality of reference samples. For each respective test sample N and each respective reference sample C, a corresponding set of coordinates 1710-1712 is embedded in a lower dimensional-space (e.g., m-space) than the dimensions of the corresponding expression profile (e.g., 1710-1, 1710-2, . . . , 1710-N, and 1712-1, 1712-2, . . . , 1712-N).

Referring to Block 1714, the method further includes evaluating the component values using the combined dataset following dimensionality reduction. The method includes determining a statistical measure of similarity between the sets of coordinates obtained for the test samples and the sets of coordinates obtained for the reference samples. Referring to Block 1716, the statistical measure of similarity is compared to a threshold value to determine if there is significant variance between the new expression dataset and the data from the existing database.

Referring to Block 1718, the new expression data set is added to the reference database when the statistical measure of similarity satisfies the threshold value. Referring to Block 1720, when the statistical measure of similarity does not satisfy the threshold value, a set of conversion factors for normalizing the expression profiles in the new expression data set against expression profiles in the reference database is determined, the expression profiles in the new expression data set are normalized using the set of conversion factors, thus obtaining a normalized new expression data set, and the normalized new expression data set is added to the reference database.

It should be noted that details of other processes described herein with respect to other methods described herein (e.g., those methods shown in FIGS. 2, 15, and 16) are also applicable in an analogous manner to the method described above with respect to FIG. 17. For example, details relating to data collection, data processing, cohort-matching, dimension-reduction analysis, etc., described above with reference to the method outlined in FIG. 17 optionally have one or more of the characteristics of the data collection, data processing, cohort-matching, dimension-reduction analysis, etc., described herein with reference to other methods described herein (e.g., those outlined in FIGS. 2, 15, and 16). For brevity, these details are not repeated here.

Example Embodiments

In some embodiments of the systems and methods described herein (e.g., the methods outlined in FIGS. 2, 15, 16, and 17, as described above), obtaining the batch dataset comprises, for each respective sample in the batch of samples obtaining, in electronic form, a corresponding plurality of sequence reads derived from the respective sample by targeted or whole transcriptome RNA sequencing, and determining, from the corresponding plurality of sequence reads, the corresponding gene expression value for each respective gene in the first set of genes. In some embodiments, the methods described herein also include a step of generating the sequencing data. However, in other aspects, the methods described herein begin after sequencing has already been performed. For example, in some embodiments, the methods described herein begin by obtaining sequence reads for each sample in a batch of samples, in electronic form, determining an expression profile for each sample in the batch of samples based on the sequence reads, and then performing a one or more quality control method, as described herein. Similarly, in some embodiments, the methods described herein begin by obtaining expression profiles, in electronic form, for each sample in a batch of samples, and then performing a one or more quality control method, as described herein.

In some embodiments, for each respective sample in the batch of samples, the corresponding plurality of sequence reads is at least 10,000 sequence reads. In some embodiments, the corresponding plurality of sequence reads is at least 100,000 sequence reads. In some embodiments, the corresponding plurality of sequence reads is at least 1,000,000 sequence reads. In some embodiments, the corresponding plurality of sequence reads is at least 10,000,000 sequence reads. In some embodiments, the corresponding plurality of sequence reads is from 10,000 to 100,000,000 sequence reads. In some embodiments, the corresponding plurality of sequence reads is from 100,000 to 50,000,000 sequence reads. In some embodiments, the corresponding plurality of sequence reads is from 1,000,000 to 50,000,000 sequence reads.

In some embodiments, the batch of test samples includes at least 10 test samples. In some embodiments, the batch of test samples includes at least 25 test samples. In some embodiments, the batch of test samples includes at least 100 test samples. In some embodiments, the batch of test samples includes at least 1000 test samples. In some embodiments, the batch of test samples includes at least 5, at least 6, at least 7, at least 8, at least 9, at least 10, at least 25, at least 50, at least 100, at least 250, at least 500, at least 750, at least 1000, at least 2500, at least 5000, at least 10,000, at least 100,000, at least 1,000,000 or more samples. In some embodiments, the batch of test samples includes from 5 to 100 test samples. In some embodiments, the batch of test samples includes from 50 to 500 test samples. In some embodiments, the batch of test samples includes from 100 to 1000 test samples. In some embodiments, the batch of test samples includes from 1000 to 100,000 test samples.

In some embodiments, the first set of genes includes at least 10 genes. In some embodiments, the first set of genes includes at least 100 genes. In some embodiments, the first set of genes includes at least 1000 genes. In some embodiments, the first set of genes includes at least 10,000 genes. In some embodiments, the batch of test samples includes at least 5, at least 6, at least 7, at least 8, at least 9, at least 10, at least 25, at least 50, at least 100, at least 250, at least 500, at least 750, at least 1000, at least 2500, at least 5000, at least 10,000, at least 20,000, at least 30,000, or more genes.

In some embodiments, the set of characteristics on which the batch and reference datasets are balanced includes at least one characteristic selected from a tissue site (the site from which the biological sample was acquired), a tumor purity, a cancer type, a sequencer identity, and a sequencing date. In some embodiments, the set of characteristics on which the batch and reference datasets are balanced includes at least two characteristics selected from a tissue site, a tumor purity, a cancer type, a sequencer identity, and a sequencing date. In some embodiments, the set of characteristics on which the batch and reference datasets are balanced includes at least three characteristics selected from a tissue site, a tumor purity, a cancer type, a sequencer identity, and a sequencing date. In some embodiments, the set of characteristics on which the batch and reference datasets are balanced includes at least a tissue site and a cancer type. In some embodiments, the set of characteristics on which the batch and reference datasets are balanced is a tissue site and a cancer type.

In some embodiments, the set of characteristics on which the batch and reference datasets are balanced includes at least one characteristic selected from a nucleic acid extraction method, a cDNA library preparation method, an RNA sequencing method, a type of reagent used, and a type of equipment used.

In some embodiments, the plurality of reference samples (the reference dataset) includes at least 50 reference samples. In some embodiments, the plurality of reference samples (the reference dataset) includes at least 100 reference samples. In some embodiments, the plurality of reference samples (the reference dataset) includes at least 500 reference samples. In some embodiments, the plurality of reference samples (the reference dataset) includes at least 1000 reference samples. In some embodiments, the plurality of reference samples (the reference dataset) includes at least 5000 reference samples. In some embodiments, the plurality of reference samples (the reference dataset) includes at least 10,000 reference samples. In some embodiments, the plurality of reference samples (the reference dataset) includes at least 100,000 reference samples. In some embodiments, the plurality of reference samples includes at least 5, at least 6, at least 7, at least 8, at least 9, at least 10, at least 25, at least 50, at least 100, at least 250, at least 500, at least 750, at least 1000, at least 2500, at least 5000, at least 10,000, at least 100,000, at least 1,000,000 or more samples. In some embodiments, the plurality of reference samples includes from 5 to 100 reference samples. In some embodiments, the plurality of reference samples includes from 50 to 500 reference samples. In some embodiments, the plurality of reference samples includes from 100 to 1000 reference samples. In some embodiments, the plurality of reference samples includes from 1000 to 100,000 reference samples.

In some embodiments, the set of reference samples balanced against a batch data set includes at least as many samples as are in the batch data set. In some embodiments, the set of reference samples balanced against a batch data set has the same number of samples as are in the batch data set. In some embodiments, the set of reference samples balanced against a batch data set includes at least 25% more samples as are in the batch data set. In some embodiments, the set of reference samples balanced against a batch data set includes at least 50% more samples as are in the batch data set. In some embodiments, the set of reference samples balanced against a batch data set includes at least 100% more samples as are in the batch data set. In some embodiments, the set of reference samples balanced against a batch data set includes at least 5-fold more samples as are in the batch data set. In some embodiments, the set of reference samples balanced against a batch data set includes at least 10-fold more samples as are in the batch data set.

The method of any one of claims 27-36, wherein the plurality of reference samples comprises at least 1000 reference samples.

In some embodiments, the aggregate value for a respective characteristic is balanced between the batch dataset and the cohort-matched reference set when the percentage of respective test samples, in the batch of test samples, having a respective value for the respective characteristic is within 2.5% of the percentage of respective reference samples, in the plurality of reference samples, having the same respective value for the respective characteristic. For instance, in some embodiments where cancer type is a characteristic being balanced between a batch dataset and a cohort-matched dataset, if the batch dataset is composed of 20% brain cancer samples, 30% lung cancer samples, and 50% colon cancer samples, the reference data set would include from 17.5% to 22.5% brain cancer samples, from 27.5% to 32.5% lung cancer samples, and from 47.5% to 52.5% colon cancer samples.

In some embodiments, the aggregate value for a respective characteristic is balanced between the batch dataset and the cohort-matched reference set when the percentage of respective test samples, in the batch of test samples, having a respective value for the respective characteristic is within 1%, within 2%, within 3%, within 4%, within 5%, within 6%, within 7%, within 8%, within 9%, within 10%, within 11%, within 12%, within 13%, within 14%, within 15%, within 16%, within 17%, within 18%, within 19%, within 20%, within 21%, within 22%, within 23%, within 24%, or within 25% of the percentage of respective reference samples, in the plurality of reference samples, having the same respective value for the respective characteristic.

In some embodiments, the dimension reduction includes embedding, for each respective test sample and each respective reference sample, the corresponding expression profile into a two-dimensional representation. In some embodiments, dimension reduction includes embedding into 2-coordinates using Uniform Manifold Approximation and Projection (UMAP). In some embodiments, the dimension reduction includes embedding, for each respective test sample and each respective reference sample, the corresponding expression profile into 2-coordinates, 3-coordinates, 4-coordinates, 5-coordinates, 6-coordinates, 7-coordinates, 8-coordinates, 9-coordinates, 10-coordinates, or more coordinates. In some embodiments, dimension reduction includes embedding into a lower-coordinate system using principal component analysis (PCA).

EXAMPLES

Example 1—Robust Detection of Sequencing Batch Effects in RNA Through Low Dimensional Embedding with Subtype Matched Reference Samples Technical batch effects, such as changes in protocols, reagents, or sequencing technology, can invalidate large scale transcriptome studies. Laboratories analyzing transcriptomes across tumor types, time, or multiple facilities must have a systematic method to validate the compatibility of data across batches.

A batch effect can manifest as a large change in a small number of genes or a small change in many genes. A robust batch effect detection method will identify either. Moreover, results from bulk RNAseq are driven by cancer type and tissue site. This complicates batch effect detection in studies across multiple cancer types. To overcome these challenges a method for evaluating technical batch effects in a heterogenous set of transcriptome samples was developed.

Briefly, samples were chosen from validated reference data to match the transcriptome set based on cancer type and tissue site. The gene expression profiles of the transcriptome set and matched reference data were embedded into 2-coordinates using Uniform Manifold Approximation and Projection (UMAP). UMAP's clustering properties are well suited for batch effect detection. Mann-Whitney U Tests were then performed on the x and y UMAP coordinates. If either test returns a p-value below a threshold, e.g., 0.01, there is likely a batch effect.

Figures 3A, 3B, 3C:
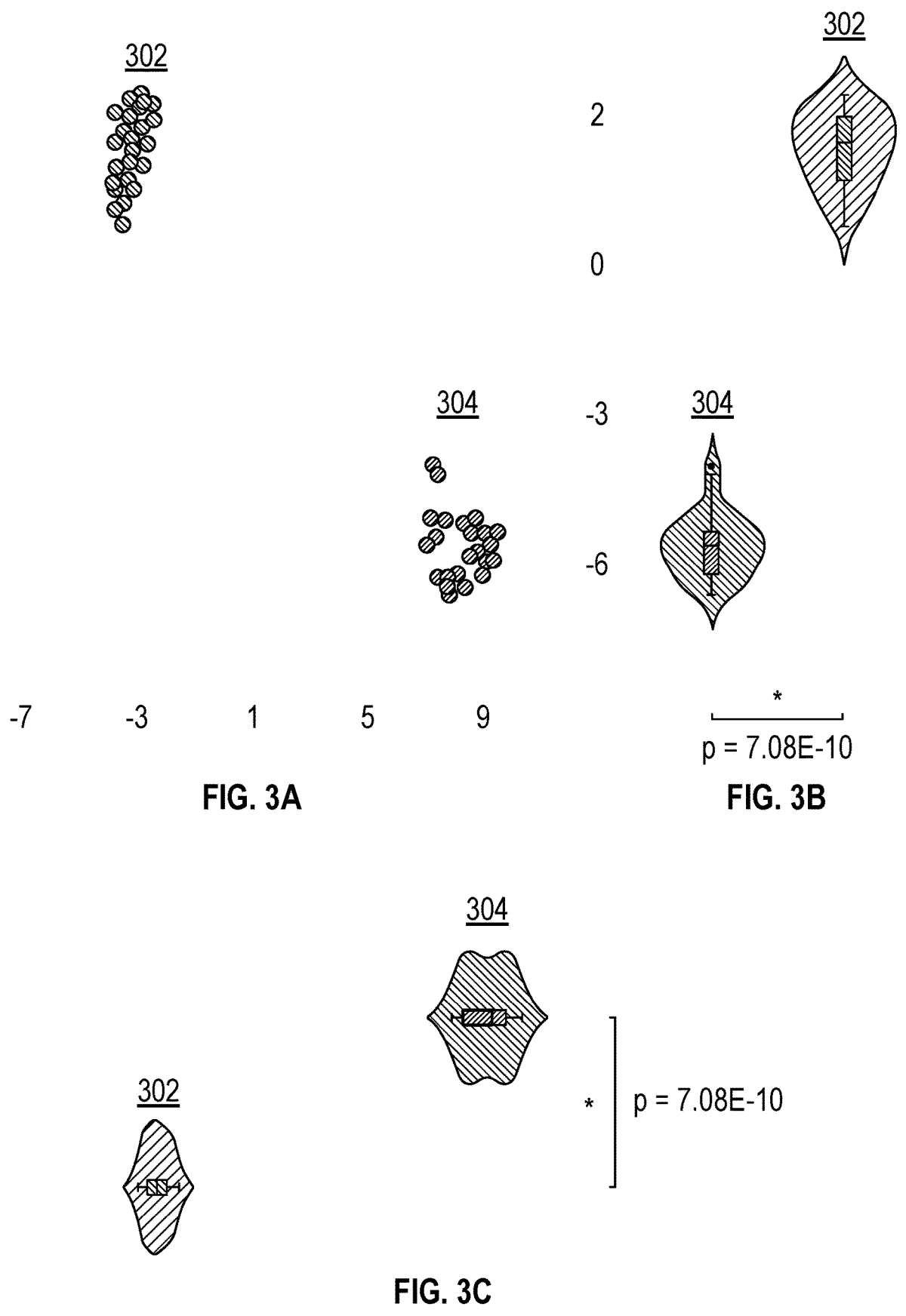

As a first example, this method was applied to determine whether batch effects are created when using different blood collection methodologies. Briefly, RNAseq data was generated for paired cohort and tissue matched blood samples collected using either PAX collection tubes or EDTA collection tubes. All other sample preparation, data collection, and data processing steps were performed the same for all samples. The RNAseq data were then embedded into 2-coordinates using UMAP (FIG. 3A; 302=PAX collection tubes; 304=EDTA collection tubes). Mann-Whitney U tests where then applied separately to the x and y coordinates of the UMAP embedding. As shown in FIGS. 3B and 3C, both Mann-Whitney U tests indicated a statistically significant difference between RNAseq data generated from blood collected in PAX collection tubes and blood collected in EDTA collection tubes (p=7.08E-10), evidencing batch effects arising from the use of different blood collection methodologies.

Figures 4A, 4B, 4C:
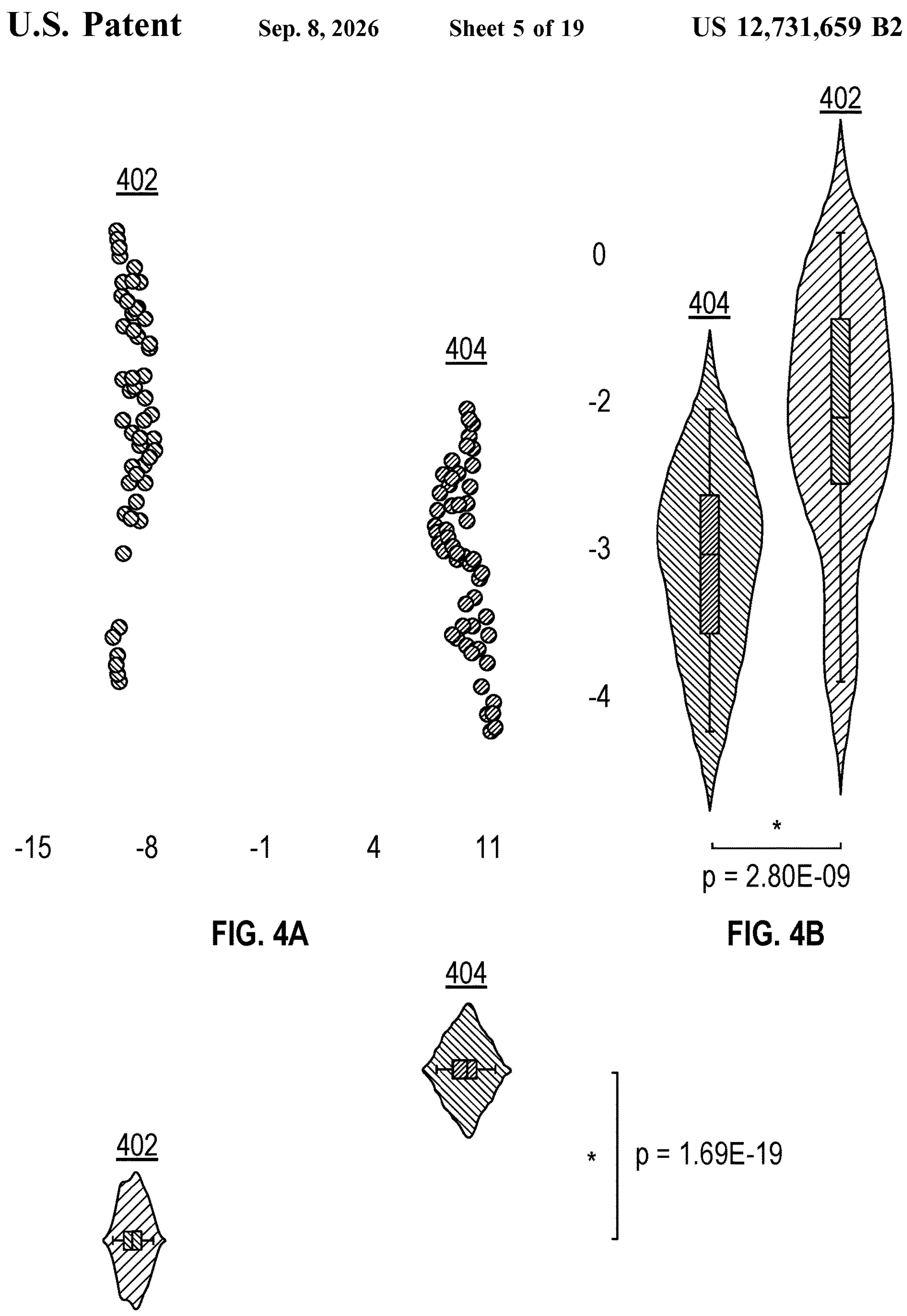
FIGS. 4A, 4B, and 4C collectively show evaluation of technical batch effects on samples aligned with Kallisto or STAR bioinformatics software pipelines, in accordance with some embodiments of the present disclosure.

As a second example, this method was applied to determine whether batch effects are created when using different bioinformatics pipelines for analysis of RNAseq data. Briefly, RNAseq data was generated for paired cohort and tissue matched samples that were either processed using the STAR pipeline or the kallisto pipeline (See, Dobin A. et al., Bioinformatics, 29(1): 15-21 (2013) (describing STAR) and Bray N L et al., Nature Biotechnology, 34:525-27 (2016) (describing kallisto). All sample preparation, data collection, and data processing steps were performed the same for all samples, except for the difference in the bioinformatics pipeline used to align the RNAseq data to quantify transcript abundance. The RNAseq data were then embedded into 2-coordinates using UMAP (FIG. 4A; 402=Star alignment; 404=kallisto alignment). Mann-Whitney U tests where then applied separately to the x and y coordinates of the UMAP embedding. As shown in FIGS. 4B and 4C, both Mann-Whitney U tests indicated a statistically significant difference between RNAseq data aligned using the STAR algorithm and RNAseq data aligned using the kallisto algorithm (p=2.80E-9 and p=1.69E-19), evidencing batch effects arising from the use of different RNAseq alignment algorithms.

Figures 5A, 5B, 5C:
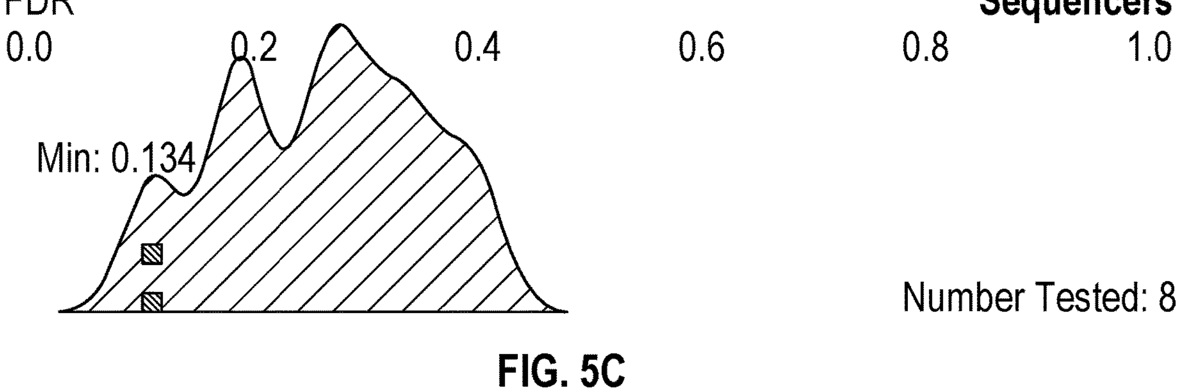
FIGS. 5A, 5B, and 5C collectively show the distribution of false discovery rates (FDRs) for common sources of technical batch effects. For each technical class-flowcell (FIG. 5A), pipeline (FIG. 5B), and sequencer (FIG. 5C)—technical batch effects were analyzed for 15 subsamples per feature and Benjamini Hochberg corrected FDRs were calculated across subsamples. The presented distributions represent the median FDR across subsamples.

Finally, the method was used to test common sources prone to technical batch effects, namely flowcells, updates to a bioinformatics pipeline, and sequencers. For each effects. For each technical class (flowcell, pipeline, and sequencer), the method was run on 15 subsamples per feature and Benjamini-Hochberg corrected false discovery rates were calculated across subsamples. The distributions presented in FIGS. 5A-5C represent the median FDR calculated across subsamples.

Thus, the method described above is an effective and easy to implement method to automatically test for technical and software batch effects across multiple cancer types and tissue sites.

Example 2—Batch Correction Applied Following Capture Probe Redesign

Capture RNA-Seq methods have a number of benefits over total mRNA capture methods, particularly when analyzing gene expression in FFPE samples. For example, polyA-selection in total mRNA capture methods perform suboptimally on FFPE samples because RNA molecules are fragmented during the fixation process. Thus, many mRNA fragments are not captured because they are no longer associated with a polyA tail. In contrast, because capture RNA-Seq methods isolate mRNA fragments using probes designed against the coding sequence of target mRNA, these methods are significantly less affected by fragmentation. In addition, capture RNA-Seq methodologies are less affected by ribosome depletion and hemoglobin depletion when using hematological samples.

However, it was observed that changes in the design of the exome-capture probes used for capture RNA-Seq results in minor technical batch effects. To correct for these batch effects, 450 samples representing a variety of cancer types that were previously exome sequenced using a first generation set of exome capture probes were selected for exome resequencing using a second generation set of exome capture probes. Linear correction factors for each gene were then determined by comparing the original exome sequencing results generated using the first generation set of exome capture probes to the new exome sequencing results generated using the second generation set of exome capture probes.

It was found that linear per-gene linear corrections were sufficient to remove all systematic differences between the two datasets. For each gene i, the corrected-to-v1 expression value $E_{ci}$ was computed as:

$$E_{ci} = (E_i * m_i) + b_i$$

where $E_i$ is the uncorrected expression level determined for gene i (log 2 TPM) using the second generation set of exome capture probes, mi is a slope correction factor for gene i, and $b_i$ is an intercept correction factor for gene i. These slope and intercept correction factors for each gene are learned to match the v1 and corrected-v2 distributions in matched datasets. This was optimized by minimizing a weighted loss function that can account for paired-sample status. By utilizing this side-information, the resulting correction factors will work robustly for sequenced samples of any cancer type, as the same linear correction can be applied to all samples processed using the second generation set of exome probes.

In order to analyze the effect of the correction factors, Principal component analysis (PCA) was performed on expression values for 100 samples, representing 37 different cancer types, that were each processed twice; once using both the first generation set of exome capture probes and once using the second generation set of exome capture probes. These 100 samples were not part of the training cohort used to generate the correction factors. PCA was first performed on uncorrected expression values determined using the second generation set of exome capture probes, and then on corrected expression values using the correction factors described above.

Figure 6A:
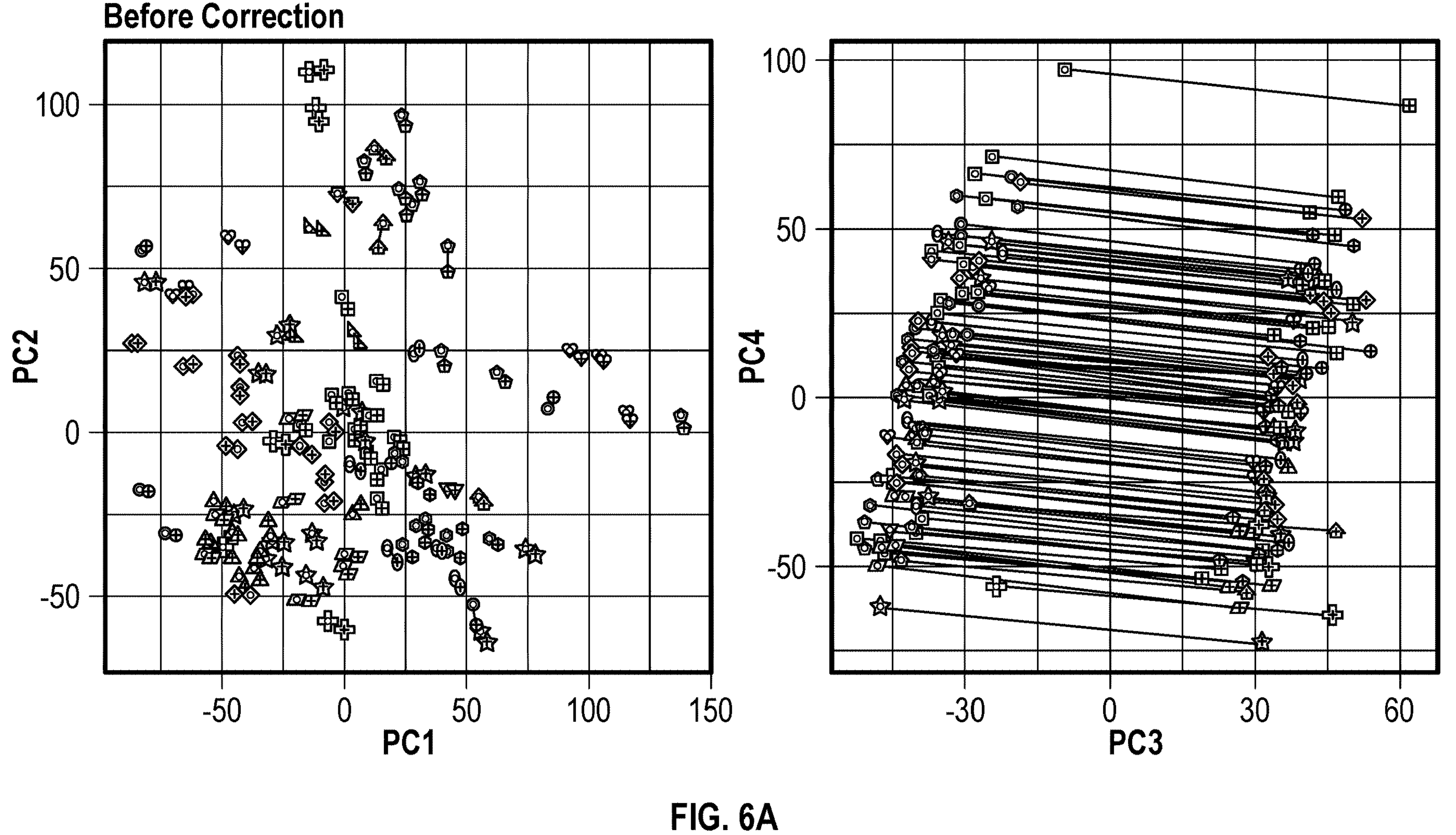
FIGS. 6A and 6B collectively illustrate the results of PCA dimension reduction analysis of approximately 100 paired cancer samples for which RNA expression was determined before and after a production change, as described in Example 2. Technical batch effects arising from the production change are identified in the third principal component term (PC3) in FIG. 6A. This technical batch effect can be removed by applying a correction factor to the RNA expression data obtained after the production change, as illustrated in FIG. 6B.
Figure 6B:
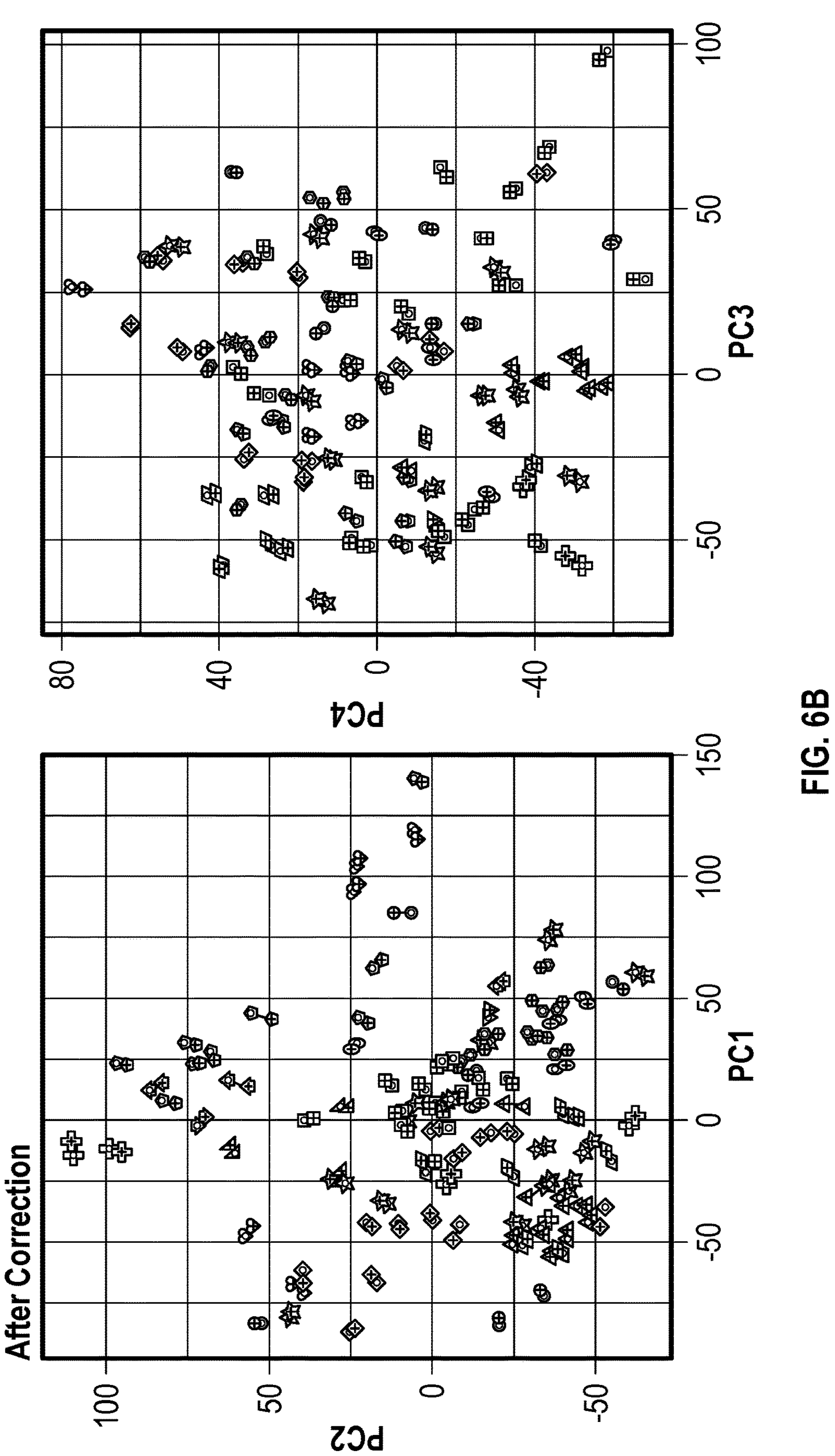

As shown in FIG. 6A, when uncorrected expression values were used for the PCA analysis, technical batch effects were clearly observable by the association of the third principal component with the assay type (+=first generation set of exome capture probes; O=second generation set of exome capture probes; lines connect paired samples). However, as shown in FIG. 6B, when uncorrected expression values were used for PCA analysis, none of the principal components were associated with assay type, and all samples clustered sample and cancer type.

Figure 7:
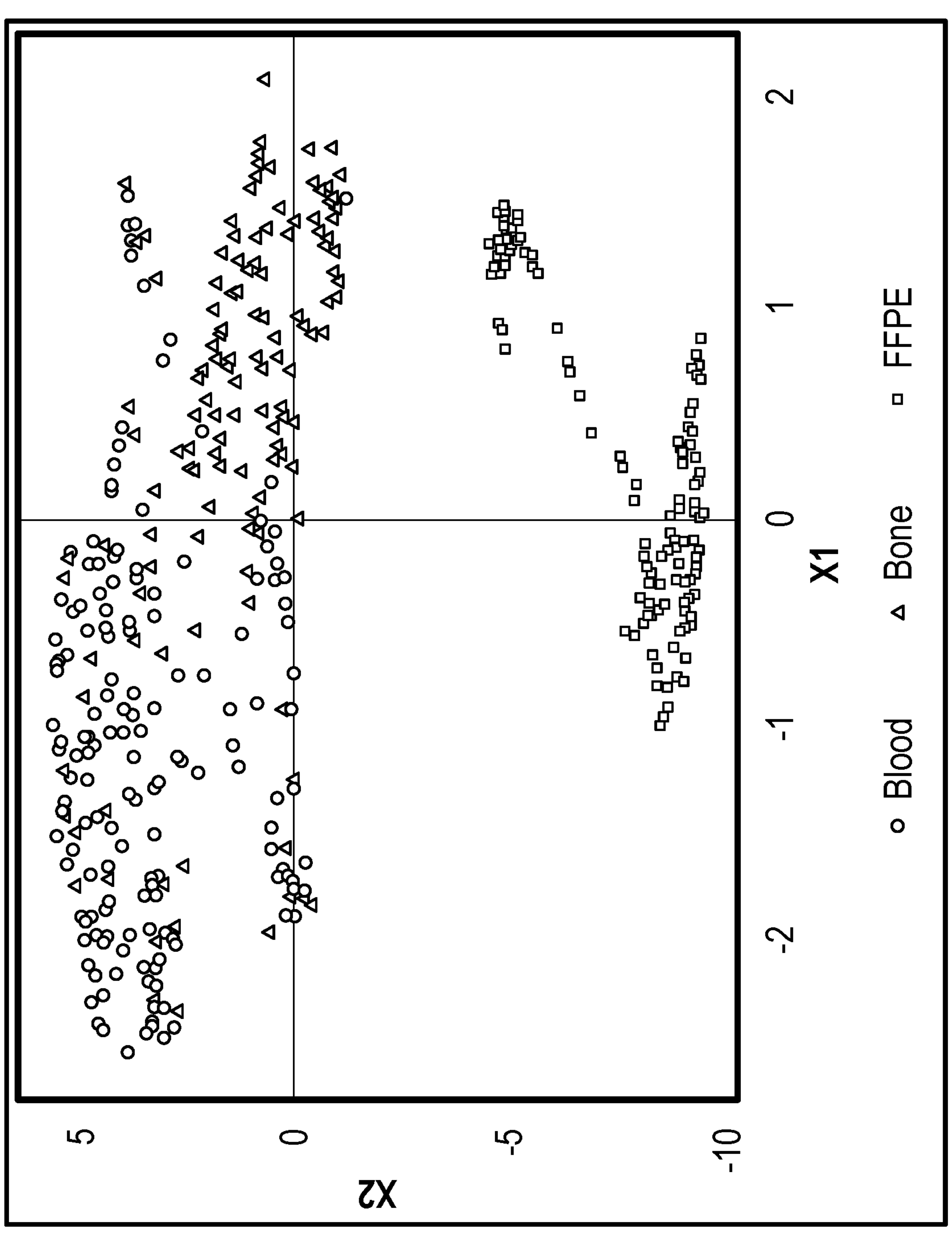
FIG. 7 illustrates UMAP embedding of transcriptome analysis of heme cancers from biological samples collected using three methodologies.

Example 3—Identification of Technical Batch Effects Arising from Differences in Biological Sample Collection Site and Preservation Method Heme cancers can be collected from whole blood, bone marrow, and sometimes preserved into Formalin-fixed paraffin-embedded (FFPE). However, the differences in these sample collection methodologies results in the introduction of technical batch effects. Briefly, RNA expression data from cohort-matched cancer samples collected either by blood sampling, bone marrow sampling, or preserved in FFPE was analyzed by dimension reduction analysis, embedded into 2-coordinates using UMAP, in accordance with some embodiments of the disclosure. The results presented in FIG. 7 illustrate that transcriptome samples are clustered and separated by FFPE versus EDTA blood/bone marrow tube on the y axis and by bone marrow vs whole on the axis. This separation is driven both by both biological and technical differences and requires a proper reference match.

Figure 8:
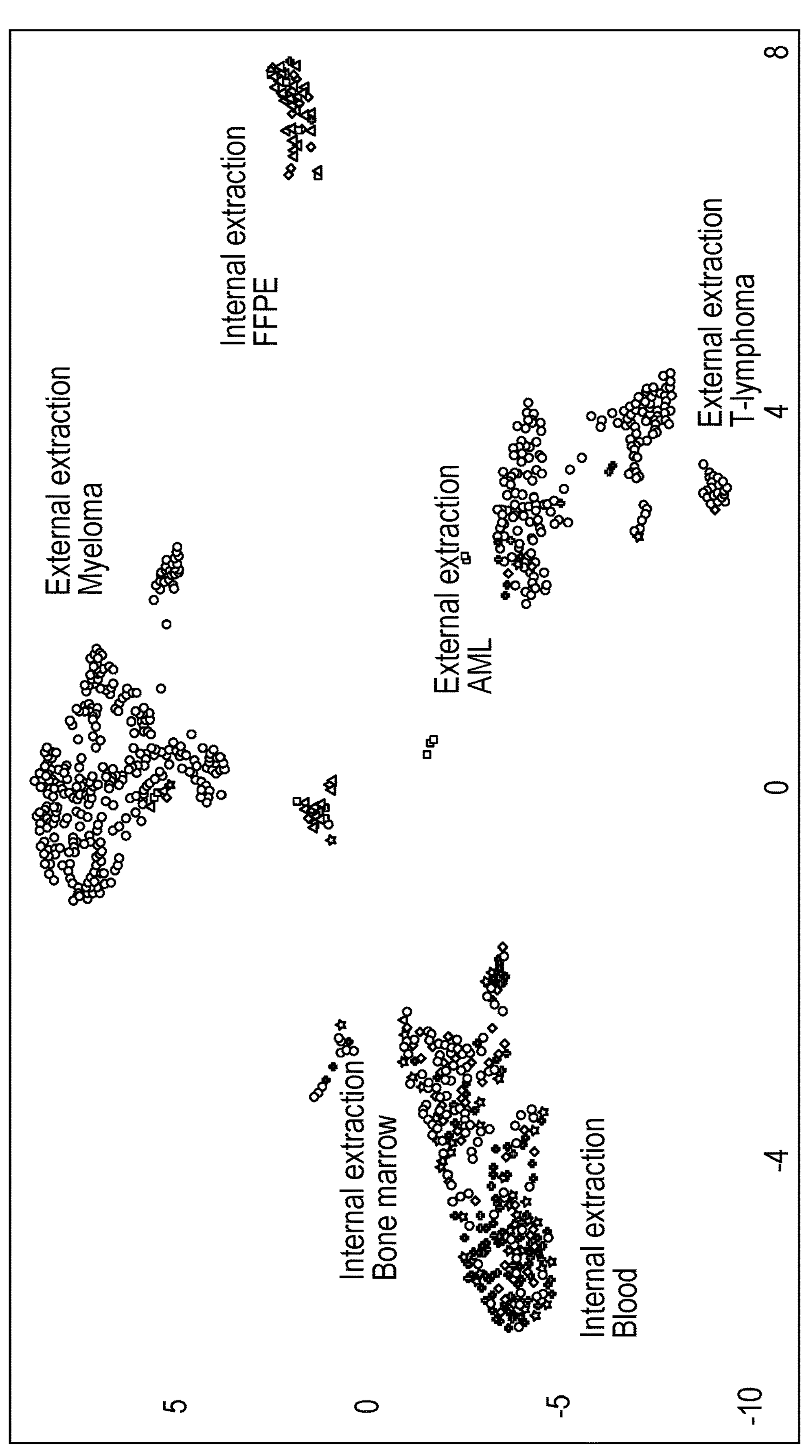
FIG. 8 illustrates UMAP embedding of transcriptome analysis of cancers from biological samples where RNA extraction was performed by the clinician or immediately before RNA sequencing.

Example 4—Identification of Technical Batch Effects Arising from Differences in the RNA Extraction Methodology Different extraction methods and chemicals used during transcriptome analysis can introduce a batch effect. For instance, batch effects can arise when the RNA samples are extracted prior to the sample being sent for sequencing (external extraction), e.g., by a clinician, as opposed to just prior to RNAseq analysis (internal extraction). Briefly, RNA expression data from cohort-matched cancer samples that were obtained before or after RNA isolation were analyzed by dimension reduction analysis, embedded into 2-coordinates using UMAP, in accordance with some embodiments of the disclosure. The results presented in FIG. 8 illustrate that heme extracted samples by an external source cluster separately from samples extracted internally. A second batch effect is observed by the separation of internal extracted FFPE samples from blood and bone marrow, as described in Example 3.

Figure 9:
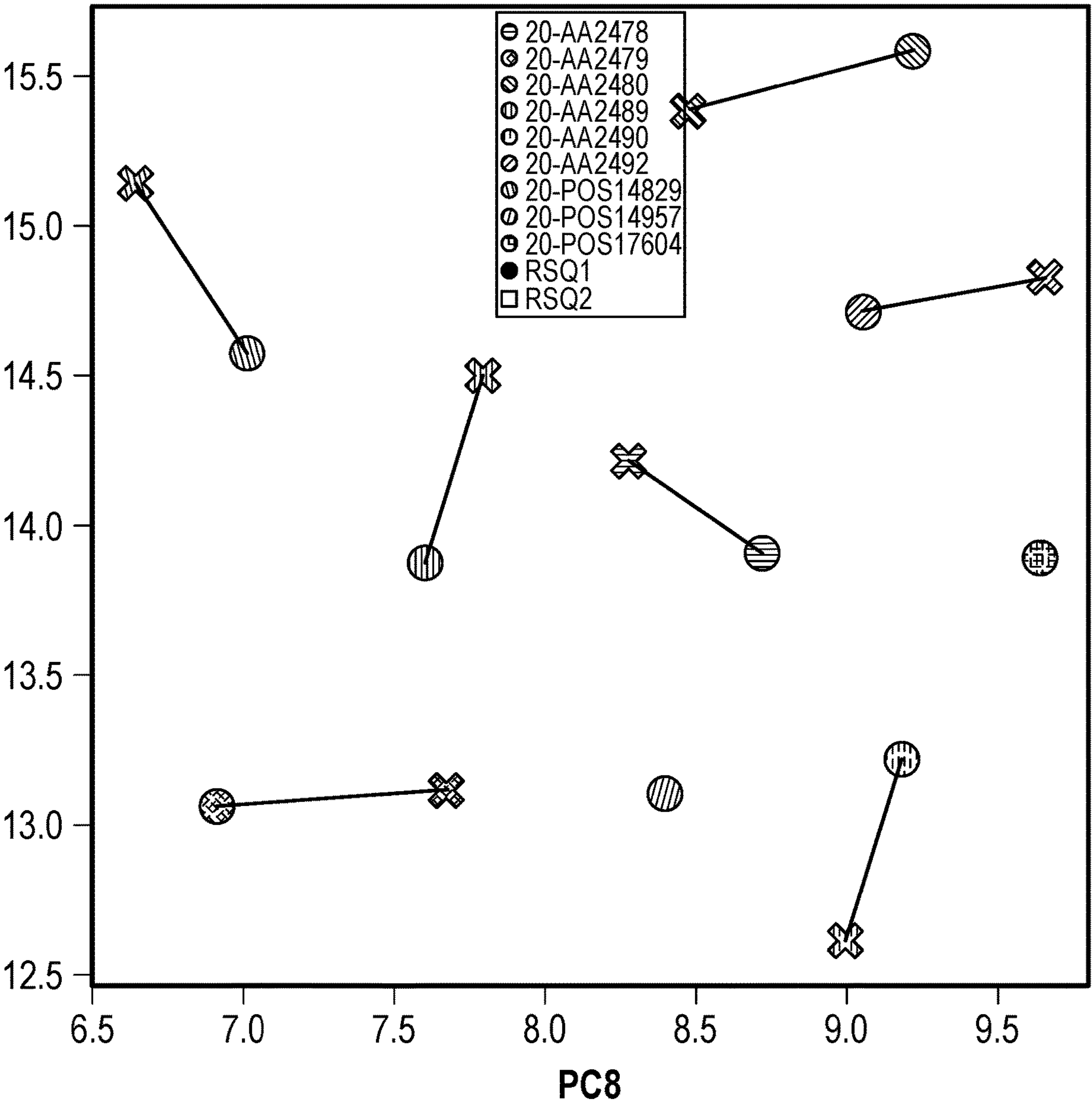
FIG. 9 illustrates PCA embedding (PC8) of transcriptome analysis of the same cancer samples using two batches of the same capture probes. Matched samples are illustrated by a line connecting the respective PC terms.

Example 5—Identification of Technical Batch Effects Arising from Different Reagent Lots Capture RNASeq methodologies includes a step where a cDNA fragment library is enriched using capture probes. In one example of this, two samples of cDNA fragment libraries prepared for several cancer samples were hybridized to two batches of the same set of biotinylated oligonucleotide probes that are complementary to genomic regions of interest. These capture probe libraries can sometimes themselves be a pool of different genomic capture designs. Manufacture probe lots and pooling of capture libraries can introduce batch effects. RNA expression data generated using both lots of capture probes were then analyzed by PCA dimension reduction analysis. The results presented in FIG. 9 illustrate a batch effect introduced by the different probe lots, detected on PC8 (x-axis).

Figure 10:
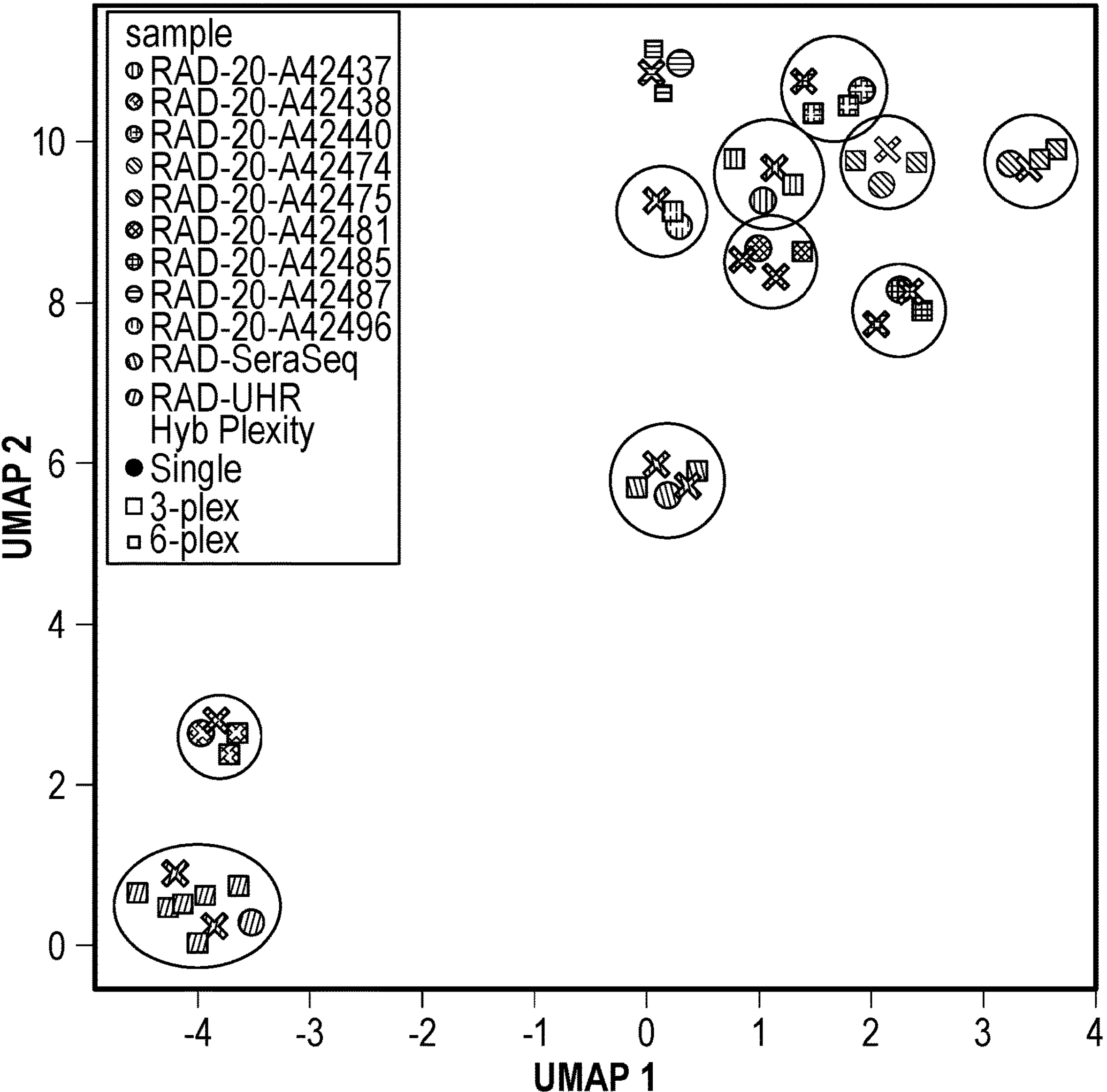
FIG. 10 illustrates UMAP embedding of transcriptome analysis of cancers performed in either of single, 3×, or 6× sample pools. Matched samples group as indicated by circles.

Example 6—Analysis of Technical Batch Effects Arising from Different Hybrid Capture Plexity Hybridization plexity refers to the number of cDNA samples pooled together during targeted capture. Assays can range from only a single sample in a pool to over a dozen. In this experiment, 9 tumor samples and 2 cell controls were sequenced under 3 plexity conditions (single, 3× and 6× sample pools). Following RNA sequencing, expression data generated using samples prepared under the different plexity conditions were analyzed by dimension reduction analysis, embedded into 2-coordinates using UMAP, in accordance with some embodiments of the disclosure. The results presented in FIG. 10 illustrate that matched samples clustered, regardless of the plexity conditions used, indicating that plexity introduces no batch effect on the transcriptome analysis.

Figure 11:
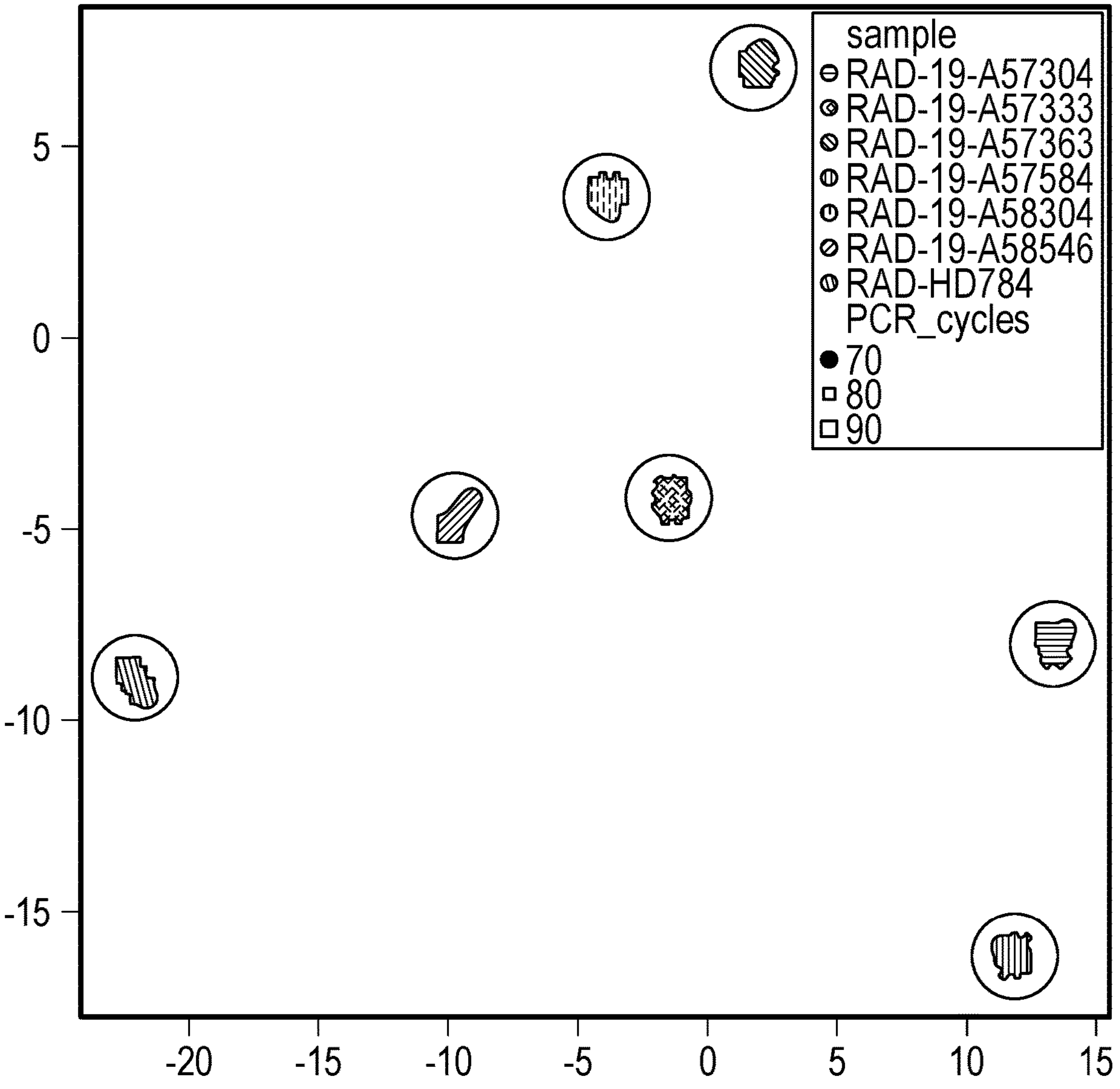
FIG. 11 illustrates UMAP embedding of transcriptome analysis of cancers performed following 7-9 PCR amplification cycles post-enrichment. Matched samples group as indicated by circles.

Example 7—Analysis of Technical Batch Effects Arising from Different Numbers of PCR Amplification Cycles In some RNAseq methodologies, post-capture PCR is an amplification step after amplicon fragments have been captured by probes, and prior to sequencing. Non-binding fragments are washed away and the remaining fragments are amplified for a set number of cycles (more cycles results in greater amplification). Too many cycles can lead to a duplication rate that is imbalanced based on the features of the sequences. In this experiment, the effect of the number of amplification cycles (between 7-9) on 6 tumors and 1 control sample was determined. Following RNA sequencing, expression data generated using samples prepared under the different amplification conditions (7-9 cycles) were analyzed by dimension reduction analysis, embedded into 2-coordinates using UMAP, in accordance with some embodiments of the disclosure. The results presented in FIG. 11 illustrate that matched samples clustered, regardless of the number of amplification cycles used, indicating that variation in the number of PCR amplification cycles between 7-9 introduces no batch effect on the transcriptome analysis.

Figure 12:
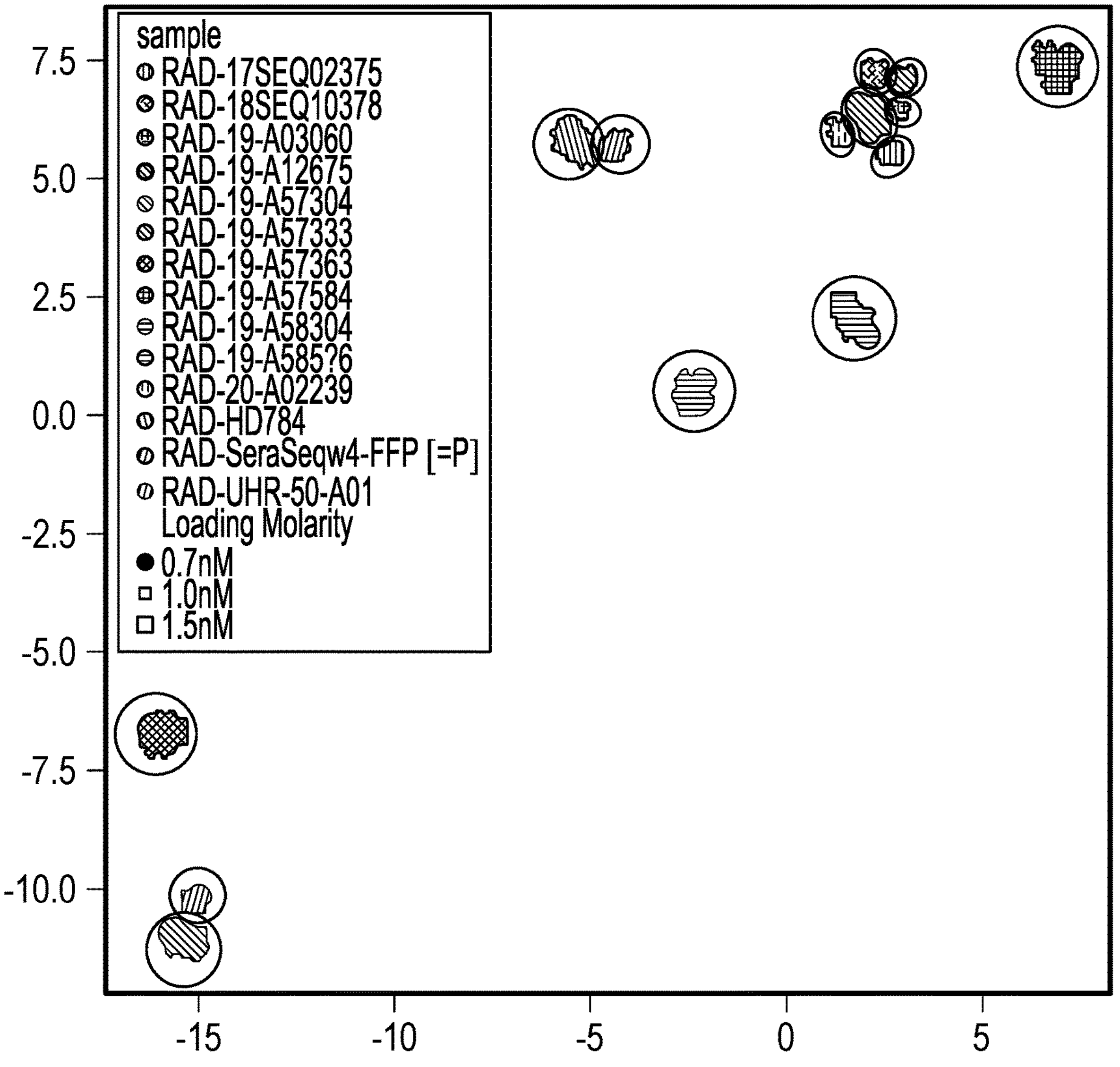
FIG. 12 illustrates UMAP embedding of transcriptome analysis of cancers performed with different sequencer load molarities (0.7 uM, 1 uM, and 1.5 uM). Matched samples group as indicated by circles.

Example 8—Analysis of Technical Batch Effects Arising from Different Sequencer Load Molarities Loading molarity refers to the amount of sample that is loaded into the sequencer. Typically, too low of a molarity can cause a higher duplication rate and noisier data. In this batch effect experiment, 11 tumor samples and 3 controls samples were sequenced under 3 molarity conditions (0.7, 1, and 1.5 uM). Following RNA sequencing, expression data generated using samples prepared under the different load molarities were analyzed by dimension reduction analysis, embedded into 2-coordinates using UMAP, in accordance with some embodiments of the disclosure. The results presented in FIG. 12 illustrate that matched samples clustered, regardless of the load molarity used, indicating that load molarity variation between 0.7 and 1.5 uM introduces no batch effect on the transcriptome analysis.

Figure 13:
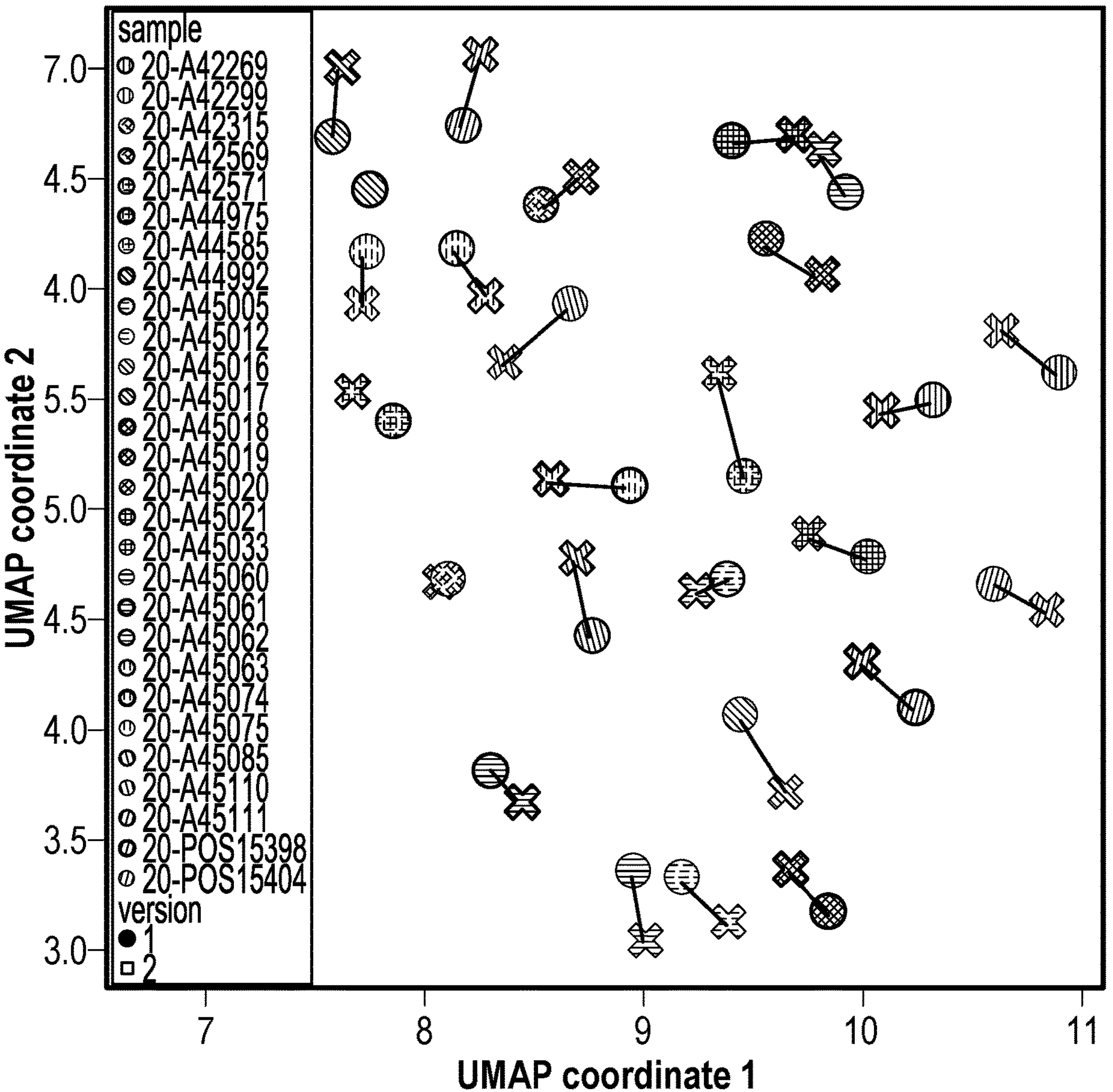
FIG. 13 illustrates UMAP embedding of transcriptome analysis of cancers performed with different sequencing reagent chemistry. Matched samples group as indicated by lines between points.
Figure 14:
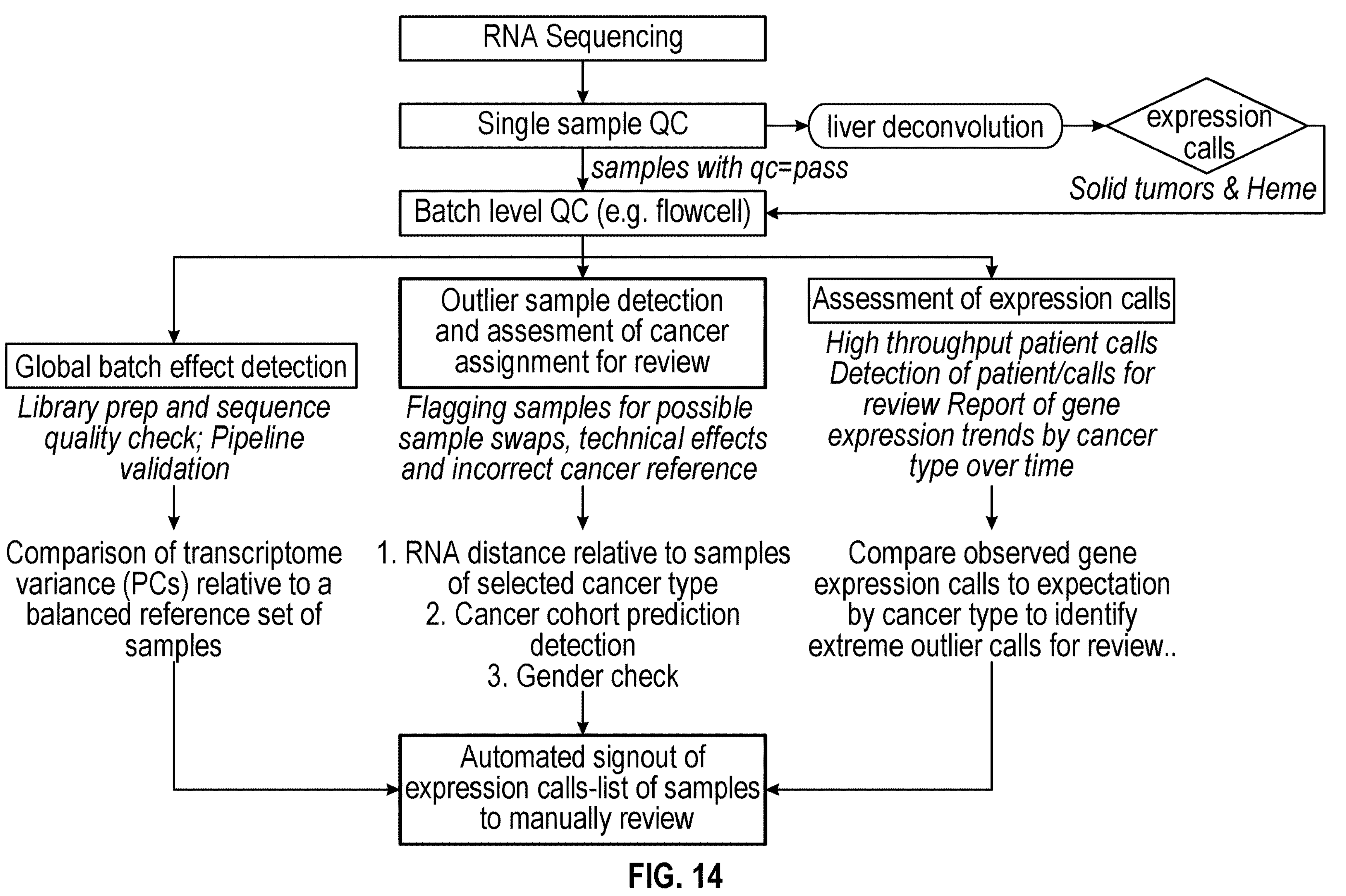
FIG. 14 illustrates an example RNA expression profiling pipeline, in accordance with some embodiments of the present disclosure.

Example 9—Analysis of Technical Batch Effects Arising from Changes in Sequencing Reagent Chemistry The change in Illumina sequencing reagents is a common, proprietary change in the chemicals used in order to better accommodate extra features to their technology. A recent example of reagent change was adapted to allow for extra reads in universal molecular indices (UMIs). In batch effect control experiment, 28 samples were sequenced under two reagent versions to verify no batch effect was detected between the previous and current versions of the reagents. Following RNA sequencing, expression data generated using samples prepared using the different versions of the reagents were analyzed by dimension reduction analysis, embedded into 2-coordinates using UMAP, in accordance with some embodiments of the disclosure. Overall, samples cluster by sample (FIG. 13; connecting line) and reagents have a minor but within acceptable range on the transcriptome variance.

CONCLUSION

The methods described herein provide improved quality control methods for evaluating batches of RNA sequencing samples. With improved accuracy and higher resolution over previous methods, the predictive algorithms provided herein can be used identify single samples and entire batches that meet quality control standards. With such increased quality control, the information used to provide patients with diagnoses and determine appropriate treatments will be more accurate, leading to improved diagnoses and more informed treatment recommendations for patients.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a non-transitory computer readable storage medium. For instance, the computer program product could contain the program modules shown in FIG. 1, and/or as described in FIGS. 2A and 2B. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method of validating a batch dataset through identification and removal of outliers from the batch dataset, the method comprising:

at a computer system having one or more processors, and memory storing one or more programs for execution by the one or more processors:

a) obtaining, in electronic form, the batch dataset comprising, for each respective biological test sample in a plurality of biological test samples, a corresponding expression profile comprising a corresponding gene expression value for each respective gene in a first set of genes, wherein obtaining the batch dataset comprises:

obtaining, in electronic form, a corresponding plurality of at least 10,000 sequence reads derived from the respective biological test sample by RNA sequencing; and determining, from the corresponding plurality of at least 10,000 sequence reads, the corresponding gene expression value for each respective gene in the first set of genes, and a corresponding set of characteristic values comprising a respective characteristic value for each respective characteristic in a first set of characteristics about the respective biological test sample;

b) determining, for the batch dataset, a reference cohort by a procedure comprising:

(i) selecting a subset of reference samples from a plurality of reference samples, wherein, each respective reference sample in the reference cohort is associated with a corresponding set of characteristic values comprising a corresponding characteristic value for each respective characteristic in a second set of characteristics about the respective reference sample, wherein the second set of characteristics comprises a third set of one or more characteristics that are also present in the first set of characteristics, (ii) determining that the percentage of respective biological test samples, in the plurality of biological test samples, having a respective value for a first characteristic in the third set of one or more characteristics, fails to be within a threshold percentage of the percentage of respective reference samples, in the subset of reference samples, having the same respective value for the first characteristic, wherein two respective biological test samples in the plurality of biological test samples have different respective values for the first characteristic and wherein the threshold percentage is five percent, (iii) determining a subset of biological test samples that cause the percentage of respective biological test samples, in the plurality of biological test samples, having a respective value for the respective characteristic to fail to be within the threshold percentage of the percentage of respective reference samples, in the subset of reference samples, having the same respective value for the first characteristic, (iv) removing the subset of biological test samples from the plurality of biological test samples, and (v) determining that the percentage of respective biological test samples, in the plurality of biological test samples, having a respective value for the respective characteristic, is within the threshold percentage of the percentage of respective reference samples, in the subset of reference samples, having the same respective value for the first characteristic;

c) obtaining, in electronic form, for each respective reference sample in the reference cohort, a corresponding expression profile comprising a corresponding gene expression value for each respective gene in the first set of genes;

d) determining (i) a first distribution for the batch dataset, with the subset of biological test samples removed from the plurality of biological test samples, using the corresponding expression profile for each respective biological test sample in the plurality of biological test samples and (ii) a second distribution for the reference cohort using the corresponding expression profile for each respective reference sample in the subset of reference samples; and e) validating the batch dataset on the basis that a comparison of the first distribution and the second distribution satisfies a comparison criterion.

2. The method of claim 1, wherein the first set of genes comprises at least 10 genes.

3. The method of claim 1, wherein the first set of genes comprises at least 10,000 genes.

4. The method of claim 1, wherein the first characteristic comprises tissue site, tumor purity, cancer type, sequencer identity, or sequencing date.

5. The method of claim 1, wherein the first characteristics comprises a nucleic acid extraction method, a cDNA library preparation method, an RNA sequencing method, a type of reagent used, or a type of equipment used.

6. The method of claim 1, wherein the reference cohort comprises at least 100 reference samples.

7. The method of claim 1, wherein the reference cohort comprises at least 1000 reference samples.

8. The method of claim 1, wherein the threshold percentage is 2.5%.

9. The method of claim 1, wherein a combined dataset is formed by a dimension reduction technique that embeds, for each respective biological test sample in the plurality of biological test samples and each respective reference sample in the reference cohort, the corresponding expression profile into a two-dimensional representation.

10. The method of claim 1, the method further comprising obtaining the at least 10,000 sequence reads by whole transcriptome RNA sequencing.

11. The method of claim 1, the method further comprising performing the first methodology by targeted panel RNA sequencing using a plurality of probes wherein each probe in the plurality of probes uniquely targets a respective portion of a reference transcriptome, and each sequence read in the corresponding plurality of sequence reads corresponds to at least one probe in the plurality of probes.

12. The method of claim 10, wherein the whole transcriptome sequencing comprises next-generation sequencing.

13. The method of claim 1, further comprising:

performing, for each respective biological test sample in the plurality of test of samples, one or more single sample quality control tests on the respective biological test sample; and removing respective biological test samples from the plurality of biological test samples that fail any one of the one or more single sample quality control tests or flagging for manual inspection respective biological test samples that fail any one of the one or more single sample quality control tests.

14. The method of claim 1, wherein the first characteristics comprises a cancer type.

15. The method of claim 1, wherein the first characteristic comprises a tissue site and a cancer type.

16. The method of claim 1, wherein the plurality of at least 10,000 sequence reads is at least 100,000 sequence reads.

17. The method of claim 1, wherein the plurality of at least 10,000 sequence reads is at least 1,000,000 sequence reads.

18. The method of claim 1, wherein each biological test sample in the plurality of biological test samples is processed through an RNA expression pipeline and the method further comprises:

rerunning the subset of biological test samples in the RNA expression pipeline.

19. A method of validating a change in an RNA expression pipeline through identification and removal of outliers from a batch dataset produced by the RNA expression pipeline, the method comprising:

at a computer system having one or more processors, and memory storing one or more programs for execution by the one or more processors:

a) obtaining, in electronic form, a batch dataset comprising, for each respective biological test sample in a plurality of biological test samples, a corresponding expression profile prepared using a first methodology, the corresponding expression profile comprising a corresponding gene expression value for each respective gene in a first set of genes, wherein obtaining the batch dataset comprises:

obtaining, in electronic form, a corresponding plurality of at least 10,000 sequence reads derived from the respective biological test sample by RNA sequencing; and determining, from the corresponding plurality of at least 10,000 sequence reads, the corresponding gene expression value for each respective gene in the first set of genes, and a corresponding set of characteristic values comprising a respective characteristic value for each respective characteristic in a first set of characteristics about the respective biological test sample;

b) determining, for the batch dataset, a reference cohort by a procedure comprising:

(i) selecting a subset of reference samples from a plurality of reference samples, wherein, each respective reference sample in the reference cohort is associated with a corresponding set of characteristic values comprising a corresponding characteristic value for each respective characteristic in a second set of characteristics about the respective reference sample, wherein the second set of characteristics comprises a third set of one or more characteristics that are also present in the first set of characteristics, (ii) determining that the percentage of respective biological test samples, in the plurality of biological test samples, having a respective value for a first characteristic in the third set of one or more characteristics, fails to be within a threshold percentage of the percentage of respective reference samples, in the subset of reference samples, having the same respective value for the first characteristic, wherein two respective biological test samples in the plurality of biological test samples have different respective values for the first characteristic and wherein the threshold percentage is five percent, (iii) determining a subset of biological test samples that cause the percentage of respective biological test samples, in the plurality of biological test samples, having a respective value for the respective characteristic to fail to be within the threshold percentage of the percentage of respective reference samples, in the subset of reference samples, having the same respective value for the first characteristic, (iv) removing the subset of biological test samples from the plurality of biological test samples, and (v) determining that the percentage of respective biological test samples, in the plurality of biological test samples, having a respective value for the respective characteristic, is within the threshold percentage of the percentage of respective reference samples, in the subset of reference samples, having the same respective value for the first characteristic;

c) obtaining, in electronic form, for each respective reference sample in the reference cohort, a corresponding expression profile comprising a corresponding gene expression value for each respective gene in the first set of genes prepared using a second methodology that is different than the first methodology;

d) determining (i) a first distribution for the batch dataset, with the subset of biological test samples removed from the plurality of biological test samples, using the corresponding expression profile for each respective biological test sample in the plurality of biological test samples and (ii) a second distribution for the reference cohort using the corresponding expression profile for each respective reference sample in the subset of reference samples; and e) validating the change in the RNA expression pipeline on the basis that a comparison of the first distribution and the second distribution satisfies a comparison criterion.

20. The method of claim 19, wherein the plurality of biological test samples comprises at least 10 biological test samples.

21. The method of claim 19, wherein the first set of genes comprises at least 10 genes.

22. The method of claim 19, wherein the first set of genes comprises at least 10,000 genes.

23. The method of claim 19, wherein the first characteristic comprises tissue site, tumor purity, cancer type, sequencer identity, or sequencing date.

24. The method of claim 19, wherein the first characteristic comprises a nucleic acid extraction method, a cDNA library preparation method, an RNA sequencing method, a type of reagent used, or a type of equipment used.

25. The method of claim 19, wherein the subset of cohort-matched reference samples comprises at least 100 reference samples.

26. The method of claim 19, wherein the subset of cohort-matched reference samples comprises at least 1000 reference samples.

27. The method of claim 19, wherein the threshold percentage is 2.5%.

28. The method of claim 19, wherein a combined dataset is formed by a dimension reduction technique that embeds, for each respective biological test sample in the plurality of biological test samples and each respective reference sample in the reference cohort, the corresponding expression profile into a two-dimensional representation.

29. The method of claim 19, the method further comprising obtaining the at least 10,000 sequence reads by a whole transcriptome RNA sequencing.

30. The method of claim 19, the method further comprising obtaining the at least 10,000 sequence reads by targeted panel RNA sequencing using a plurality of probes, wherein each probe in the plurality of probes uniquely targets a respective portion of a reference transcriptome, and each sequence read in the corresponding plurality of sequence reads corresponds to at least one probe in the plurality of probes.

31. The method of claim 29, wherein the whole transcriptome sequencing comprises next-generation sequencing.

32. The method of claim 19, further comprising:

performing, for each respective biological test sample in the batch of test of samples, one or more single sample quality control tests on the respective biological test sample; and removing respective biological test samples from the plurality of biological test samples that fail any one of the one or more single sample quality control tests or flagging for manual inspection respective biological test samples that fail any one of the one or more single sample quality control tests.

33. The method of claim 19, wherein the first characteristic comprises a cancer type.

34. The method of claim 19, wherein the first characteristic comprises a tissue site and a cancer type.

35. The method of claim 19, wherein the plurality of at least 10,000 sequence reads is at least 100,000 sequence reads.

36. The method of claim 19, wherein the plurality of at least 10,000 sequence reads is at least 1,000,000 sequence reads.

37. The method of claim 19, wherein each biological test sample in the plurality of biological test samples is processed through the RNA expression pipeline and the method further comprises:

rerunning the subset of biological test samples in the RNA expression pipeline.

38. A method of adding RNA expression data to a reference database comprising a plurality of reference database samples, the method comprising:

at a computer system having one or more processors, and memory storing one or more programs for execution by the one or more processors:

a) obtaining, in electronic form, an expression dataset comprising, for each respective biological test sample in a plurality of biological test samples, a corresponding expression profile comprising a corresponding gene expression value for each respective gene in a first set of genes, wherein generating the profile comprises:

obtaining, in electronic form, a corresponding plurality of at least 10,000 sequence reads derived from the respective biological test sample by RNA sequencing; and determining, from the corresponding plurality of at least 10,000 sequence reads, the corresponding gene expression value for each respective gene in the first set of genes, and a corresponding set of characteristic values comprising a respective characteristic value for each respective characteristic in a first set of characteristics about the respective biological test sample;

b) determining for the expression dataset, a reference cohort by a procedure comprising:

(i) selecting a subset of reference samples from a plurality of reference samples, wherein, each respective reference sample in the reference cohort is associated with a corresponding set of characteristic values comprising a corresponding characteristic value for each respective characteristic in a second set of characteristics about the respective reference sample, wherein the second set of characteristics comprises a third set of one or more characteristics that are also present in the first set of characteristics, (ii) determining that the percentage of respective biological test samples, in the plurality of biological test samples, having a respective value for a first characteristic in the third set of one or more characteristics, fails to be within a threshold percentage of the percentage of respective reference samples, in the subset of reference samples, having the same respective value for the first characteristic, wherein two respective biological test samples in the plurality of biological test samples have different respective values for the first characteristic and wherein the threshold percentage is five percent, (iii) determining a subset of biological test samples that cause the percentage of respective biological test samples, in the plurality of biological test samples, having a respective value for the respective characteristic to fail to be within the threshold percentage of the percentage of respective reference samples, in the subset of reference samples, having the same respective value for the first characteristic, (iv) removing the subset of biological test samples from the plurality of biological test samples, and (v) determining that the percentage of respective biological test samples, in the plurality of biological test samples, having a respective value for the respective characteristic, is within the threshold percentage of the percentage of respective reference samples, in the subset of reference samples, having the same respective value for the first characteristic;

c) obtaining, in electronic form, for each respective reference sample in the reference cohort, a corresponding profile comprising a corresponding gene expression value for each respective gene in the first set of genes, each profile corresponding to a reference sample in the subset of reference samples is from the reference database, and d) determining (i) a first distribution for the expression dataset, with the subset of biological test samples removed from the plurality of biological test samples, using the corresponding expression profile for each respective biological test sample in the plurality of biological test samples and (ii) a second distribution for the reference cohort using the corresponding expression profile for each respective reference sample in the subset of reference samples; and e) adding the expression dataset to the reference database when a comparison of the first distribution and the second distribution satisfies a comparison criterion, or when the comparison does not satisfy the comparison criterion:

determining a set of conversion factors for standardizing the expression profiles in the expression dataset against expression profiles in the reference database, standardizing the expression profiles in the expression dataset using the set of conversion factors, thereby obtaining a standardized expression dataset, and adding the standardized expression dataset to the reference database.

39. The method of claim 38, wherein the plurality of biological test samples comprises at least 10 biological test samples.

40. The method of claim 38, wherein the first set of genes comprises at least 10 genes.

41. The method of claim 38, wherein the first set of genes comprises at least 10,000 genes.

42. The method of claim 38, wherein the first characteristic is tissue site, tumor purity, cancer type, sequencer identity, or sequencing date.

43. The method of claim 38, wherein the first characteristic is a nucleic acid extraction method, a cDNA library preparation method, an RNA sequencing method, a type of reagent used, or a type of equipment used.

44. The method of claim 38, wherein the subset of reference samples comprises at least 100 reference samples.

45. The method of claim 38, wherein the subset of reference samples comprises at least 1000 reference samples.

46. The method of claim 38, wherein the threshold percentage is 2.5%.

47. The method of claim 38, wherein a combined dataset is formed by a dimension reduction technique that embeds, for each respective biological test sample in the plurality of biological test samples and each respective reference sample in the subset of reference samples, the corresponding expression profile into a two-dimensional representation.

48. The method of claim 38, the method further comprising obtaining the at least 10,000 sequence reads by a whole transcriptome RNA sequencing.

49. The method of claim 38, the method further comprising obtaining the at least 10,000 sequence reads by targeted panel RNA sequencing using a plurality of probes, wherein each probe in the plurality of probes uniquely targets a respective portion of a reference transcriptome, and each sequence read in the corresponding plurality of sequence reads corresponds to at least one probe in the plurality of probes.

50. The method of claim 48, wherein the whole transcriptome sequencing comprises next-generation sequencing.

51. The method of claim 38, further comprising:

performing, for each respective biological test sample in the plurality of biological test samples, one or more single sample quality control tests on the respective biological test sample; and removing respective biological test samples from the plurality of biological test samples that fail any one of the one or more single sample quality control tests or flagging for manual inspection respective biological test samples that fail any one of the one or more single sample quality control tests.

52. The method of claim 38, wherein the first characteristic comprises a cancer type.

53. The method of claim 38, wherein the first characteristic comprises a tissue site and a cancer type.

54. The method of claim 38, wherein the plurality of at least 10,000 sequence reads is at least 100,000 sequence reads.

55. The method of claim 38, wherein the plurality of at least 10,000 sequence reads is at least 1,000,000 sequence reads.

56. The method of claim 38, wherein each biological test sample in the plurality of biological test samples is processed through an RNA expression pipeline and the method further comprises:

rerunning the subset of biological test samples in the RNA expression pipeline.

57. A method of processing a batch dataset, the method comprising:

a) obtaining using a computer system, in electronic form, the batch dataset comprising, for each respective biological test sample in a plurality of biological test samples, a corresponding expression profile comprising a corresponding gene expression value for each respective gene in a first set of genes, wherein obtaining the batch dataset comprises:

obtaining, in electronic form, a corresponding plurality of at least 10,000 sequence reads derived from the respective biological test sample by RNA sequencing; and determining, from the corresponding plurality of at least 10,000 sequence reads, the corresponding gene expression value for each respective gene in the first set of genes, and a corresponding set of characteristic values comprising a respective characteristic value for each respective characteristic in a first set of characteristics about the respective biological test sample;

b) determining, for the batch dataset, a reference cohort by a procedure comprising:

(i) selecting, using a computer system, a subset of reference samples from a plurality of reference samples, wherein, each respective reference sample in the reference cohort is associated with a corresponding set of characteristic values comprising a corresponding characteristic value for each respective characteristic in a second set of characteristics about the respective reference sample, wherein the second set of characteristics comprises a third set of one or more characteristics that are also present in the first set of characteristics, (ii) determining, using a computer system, that the percentage of respective biological test samples, in the plurality of biological test samples, having a respective value for a first characteristic in the third set of one or more characteristics, fails to be within a threshold percentage of the percentage of respective reference samples, in the subset of reference samples, having the same respective value for the first characteristic, wherein two respective biological test samples in the plurality of biological test samples have different respective values for the first characteristic and wherein the threshold percentage is five percent, (iii) determining, using a computer system, a subset of biological test samples that cause the percentage of respective biological test samples, in the plurality of biological test samples, having a respective value for the respective characteristic to fail to be within the threshold percentage of the percentage of respective reference samples, in the subset of reference samples, having the same respective value for the first characteristic, c) obtaining using a computer system, in electronic form, for each respective reference sample in the reference cohort, a corresponding expression profile comprising a corresponding gene expression value for each respective gene in the first set of genes;

d) determining, using a computer system, (i) a first distribution for the batch dataset, with the subset of biological test samples removed from the plurality of biological test samples, using the corresponding expression profile for each respective biological test sample in the plurality of biological test samples and (ii) a second distribution for the reference cohort using the corresponding expression profile for each respective reference sample in the subset of reference samples; and e) validating, using a computer system, the batch dataset on the basis that a comparison of the first distribution and the second distribution satisfies a comparison criterion, wherein each biological test sample in the plurality of biological test samples is processed through an RNA expression pipeline and the method further comprises:

rerunning the subset of biological test samples in the RNA expression pipeline.

* * * * *